US006329347B1

(12) United States Patent
Phillips et al.

(10) Patent No.: US 6,329,347 B1
(45) Date of Patent: *Dec. 11, 2001

(54) COMPOSITION AND METHOD FOR THE TREATMENT OF BLADDER CANCER

(75) Inventors: Nigel C. Phillips, Pointe Claire; Mario C. Filion, Montreal, both of (CA)

(73) Assignee: Bioniche Life Sciences Inc., Belleville (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/129,313

(22) Filed: Aug. 5, 1998

Related U.S. Application Data

(60) Provisional application No. 60/054,777, filed on Aug. 5, 1997, provisional application No. 60/075,111, filed on Feb. 18, 1998, provisional application No. 60/075,067, filed on Feb. 18, 1998, and provisional application No. 60/086,317, filed on May 21, 1998.

(51) Int. Cl.$^7$ .......................... A01N 63/00; A01N 61/00; A01N 43/04; C12N 1/12; C07H 21/02

(52) U.S. Cl. ............................. 514/44; 514/1; 424/93.2; 424/93.4; 435/243; 435/251.3; 536/23.1

(58) Field of Search ....................... 514/1, 44; 435/253.1, 435/243; 536/23.1

(56) References Cited

U.S. PATENT DOCUMENTS

| | | | |
|---|---|---|---|
| 3,172,815 | 3/1965 | Fax et al. | 167/78 |
| 3,976,544 | 8/1976 | Adam et al. | 195/2 |
| 4,010,257 | 3/1977 | Adlam et al. | 424/92 |
| 4,036,953 | 7/1977 | Adam et al. | 424/92 |
| 4,152,423 | 5/1979 | Adam et al. | 424/92 |
| 4,182,751 | 1/1980 | Ayme | 424/92 |
| 4,337,243 | 6/1982 | Ayme | 424/92 |
| 4,520,019 | 5/1985 | Ribi et al. | 424/195.1 |
| 4,579,941 | 4/1986 | Furutani et al. | 536/27 |
| 4,647,456 | 3/1987 | Pulverer | 424/95 |
| 4,663,306 | 5/1987 | Cantrell | 514/2 |
| 4,724,144 | 2/1988 | Rook et al. | 424/88 |
| 4,726,947 | 2/1988 | Shimada et al. | 424/92 |
| 4,744,984 | 5/1988 | Ragland | 424/92 |
| 4,877,611 | 10/1989 | Cantrell | 424/88 |
| 5,759,554 | 6/1998 | Alkemade et al. | 424/282.1 |

FOREIGN PATENT DOCUMENTS

99/07383    2/1999    (WO).

OTHER PUBLICATIONS

Verma et al., Nature, vol. 389, pp. 239–242, Sep. 1997.*
Eck et al., Goodman & Gilman's The Pharmacological Basis of Therapeutics, Chapter 5: Gene Based Therapy, Ninth Edition, McGraw–Hill, New York, pp. 77–101, 1996.*
Filion, M.C. et al., "Mycobacterial cell wall—DNA complex induces apoptosis in cancer cells," *J. Pharm. Pharmacol.*, vol. 50 (Supplement), p. 39 (1998).

Filion, M.C. et al., "*Mycobacterium phlei* wall complex directly induces apoptosis in human bladder cancer cells," *British J. of Cancer*, vol. 79, No. 2, pp. 229–235 (1999).

Morales, A., et al., "Immunotherapy of an Experimental Adenocarcinoma of the Prostate," *J. of Urology*, vol. 153, pp. 1706–1710 (May 1995).

E. Marshal, Science, vol. 269, pp. 1052–1053, Aug. 1995.*

Gray, G.R., et al., "Brief Communication: Immunotherapy of Cancer: Tumor Suppression and Regression by Cell Walls of *Mycobacterium phlei* Attached to Oil Droplets," *J. Natl. Cancer Instit.*, vol. 55, No. 3, pp. 727–730 (Sep. 1975).

Tokunaga, T. et al., "Synthetic Oligonucleotides with Particular Base Sequences from the cDNA Encoding Proteins of *Mycobacterium bovis* BCG Induce Interferons and Activate Natural Killer Cells," *Microbiol. Immunol.*, vol. 36, No. 1, pp. 55–66 (1992).

Pisetsky, D.S., et al., "Stimulation of in vitro proliferation of murine lymphocytes by synthetic oligodeoxynucleotides," *Mol. Biol. Reports*, vol. 18, pp. 217–221 (1993).

Pisetsky, D.S., et al.,Immune Activation by Bacterial DNA: A New Genetic Code, *Immunity*, vol. 5, pp. 303–310, (Oct. 1996).

Klinman, D.M. et al., "CpG motifs present in bacterial DNA rapidly induce lymphocytes to secrete interleukin 6, internleukin 12, and interferon γ," *Proc. Natl. Acad. Sci. USA*, vol. 93, pp. 2879–2883 (Apr. 1996).

Chin, J.L. et al., "Mycobacterium Cell Wall: An Alternate to Intravesical Bacillus Calmetter Guerin (BCG) Therapy in Orthotopic Murine Bladder Cancer," *J. Urology*, vol. 156, pp. 1189–1193 (Sep. 1996).

* cited by examiner

*Primary Examiner*—Karen M. Hauda
*Assistant Examiner*—Shin-Lin Chen
(74) *Attorney, Agent, or Firm*—Kilpatrick Stockton LLP

(57) ABSTRACT

The present invention relates to a composition and method useful for treating cancer in the urinary bladder. The present invention particularly relates to a composition comprising a *Mycobacterium phlei* deoxyribonucleic acid (M-DNA)-*Mycobacterium phlei* cell wall complex (MCC), wherein the M-DNA is preserved and complexed on the *Mycobacterium phlei* cell wall, and a pharmaceutically acceptable carrier. The MCC composition inhibits proliferation of and induces apoptosis in cancer cells in the urinary bladder and stimulates the responsive cells of the immune system to produce cytokines and reactive oxygen species. Methods of making MCC and methods of using MCC also are disclosed.

24 Claims, 23 Drawing Sheets

US 6,329,347 B1

COMPOSITION AND METHOD FOR THE TREATMENT OF BLADDER CANCER

CROSS REFERENCE TO RELATED APPLICATIONS

This application claims priority to U.S. Provisional Application Ser. No. 60/054,777, filed Aug. 5, 1997 and U.S. Provisional Application Ser. No. 60/075,111, filed Feb. 18, 1998, and U.S. Provisional Application No. 60/075,067, filed Feb. 18, 1998, and U.S. Provisional Application Ser. No. 60/086,317, filed May 21, 1998.

FIELD OF INVENTION

The present invention relates to a composition and method useful for treating cancer in the urinary bladder of an animal, including a human, comprising a mycobacterial deoxyribonucleic acid (B-DNA)-mycobacterial cell wall complex (BCC), wherein the B-DNA is preserved and complexed on the bacterial cell wall, such that the BCC is effective for treating bladder cancer. More particularly, the present invention relates to a *Mycobacterium phlei* DNA (M-DNA)-*Mycobacterium phlei* cell wall complex (MCC), wherein the M-DNA is preserved and complexed on the *M. phlei* cell wall, such that the MCC is effective in inhibiting proliferation of and inducing apoptosis in bladder cancer cells, and in stimulating responsive cells of the immune system to produce bioactive molecules. Methods of making MCC and methods of using MCC also are disclosed.

BACKGROUND OF THE INVENTION

Cancer is an aberrant net accumulation of atypical cells, which can result from an excess of proliferation, an insufficiency of apoptosis, or a combination of the two. Apoptosis is a genetically programmed, non-inflammatory, energy-dependent form of cell death in tissue, including adult tissue (Steller H. Science 267:1445–1449, 1995), and is associated with nuclear DNA-fragmentation, release of nuclear matrix proteins (NuMA), and loss of cell substrate contact.

Apoptosis can be initiated by ligands which bind to cell surface receptors including, but not limited to, Fas (CD95) (French et al. Journal of Cell Biology 133:355–364, 1996) and tumor necrosis factor receptor 1 (TNFR1). FasL binding to Fas and TNF binding to TNFR1 initiate intracellular signaling resulting in the activation of cysteine aspartyl proteases (caspases), which initiate the lethal proteolytic cascade of apoptosis execution (Muzio et al. Cell 85:817–827, 1996). Mutations in Fas or in TNFR1 can cause a failure of apoptosis.

Apoptosis also can be induced by intracellular proteins including, but not limited to, p53/p21 regulators (Levine A. Cell 88:323–331, 1997). p53/p21 act as transcription factors to activate expression of apoptosis-mediating genes, including, but not limited to, genes encoding proteins that generate free radicals that, it turn, damage the cell's mitochondria, whose contents leak out into the cytoplasm and activate apoptotic caspases (Polyak et al. Nature 389:300–305, 1997). Loss of functional p53/p21 correlates with aggressiveness in a variety of cancers (Fisher D. Cell 78:529–542, 1994).

Resistance to apoptosis induction has emerged as an important category of multiple drug resistance (MDR), one that likely explains a significant proportion of treatment failures. MDR, the simultaneous resistance to structurally and functionally unrelated chemotherapeutic agents, can be both inherent and acquired. That is, some cancers never respond to therapy, whereas other cancers, initially sensitive to therapy, develop drug resistance. As chemotherapeutic agents rely primarily on induction of apoptosis in cancer cells for their therapeutic effect, drug resistance, which diminishes the effectiveness of chemotherapeutic agents, leads directly or indirectly to reduced apoptosis and is generally associated with poor prognosis in a variety of cancers.

Cancer of the bladder is particularly difficult to treat successfully (Lamm et al. Journal of Urology 153:1444–1450, 1995). Live bacillus Calmette-Guerin (BCG) has been shown to have activity against bladder cancer cells in vivo (Morales A. Journal of Urology 132:457–459, 1984) and in vitro (Jackson et al. International Journal of Oncology 5:697–703, 1994; Pryor et al. Cancer Immunology and Immunotherapy 41:309–316, 1995; Pryor et al. British Journal of Cancer 71:801–807, 1995). However, live BCG can cause serious side effects including, but not limited to, fever, serum sickness-like syndromes, granulomatous infection, sepsis and even death (Lamm et al. Journal of Urology 147:596–600, 1992). Moreover, variability in the immunogenicity and in the stability of both live BCG and heat-killed BCG make its use difficult and unpredictable.

Although BCG inhibits proliferation of bladder cancer cells, it does not directly induce apoptosis (Sasaki et al. Urology International 59:142–148, 1997), but does stimulate lymphocyte activated killer (LAK) cells and lymphocyte production of bioactive molecules (Kudoh et al. British Journal of Urology 80S2:40, 1997). Human bladder T24 cancer cells will undergo apoptosis after contact with LAK cells (Shemtov et al. Journal of Urology 154:269–274, 1995) and, will undergo apoptosis and cytolysis in the presence of bioactive molecules.

Cytolysis is the complete or partial destruction of a cell and is mediated by the immune system. As used herein, the immune system includes macrophages, monocytes, lymphocytes and leukocytes. Macrophages and monocytes in the bladder wall accumulate around tumor islands in patients with bladder cancer (El-Demiry et al. British Journal of Urology 58:436–442, 1986; loachim-Velogiammi et al. Journal of Pathology 174:183–189, 1994) and, when stimulated, produce bioactive molecules. By produce is meant synthesize and secrete. These bioactive molecules include, but are not limited reactive oxygen species and cytokines.

Reactive oxygen species include, but are not limited, to nitric oxide, superoxide radicals and hydroxyl radicals. Reactive oxygen species induce cytolysis and apoptosis in susceptible target cells. Cytokines include, but are not limited to, interleukin-1 (IL-1), interleukin-6 (IL-6), interleukin-10 (IL-10), interleukin-12 (IL-12), and GM-CSF. IL-12 is reported to have anti-cancer activity toward some cancer cell lines (Stine et al. Annals NY Academy of Science 795:420–421; 1996; Angillo et al. Annals NY Academy of Sciences 795:158–165, 1996; Chen et al. Journal of Immunology 159:351–359, 1997), whereas GM-CSF is reported to have pro-cancer activity toward some cancer cell lines (Hawkyard et al. Journal of Urology 150:514–518, 1993).

Preparations of bacterial origin, including, but not limited to, preparations from Mycobacterium species, have been used to treat cancers (U.S. Pat. No. 4,503,048). REGRESSIN®, a non-viable mycobacterial cell wall extract (MCWE) formulated as a mineral oil emulsion (Bioniche, Inc. London, Ontario, Canada), has been shown to reduce cancer burden in bladder cancers (Kadhim et al. Journal of Urology 149:A255, 1996; Morales et al. Journal of Urology 157:A214, 1997). MCWE is composed primarily of peptidoglycan and glycolipid (Chin et al. Journal of Urology 156:1189–1193, 1996) and contain N-acetylmuramyl-L-alanyl-D-isoglutamine (muramyl dipeptide) and mycolic acid derivatives. Both muramyl dipeptide and mycolic acid derivatives stimulate the immune system by activation of macrophage and monocyte mediated reactions (Mallick et al. Comparative Immunology and Microbiology of Infectious Diseases 8:55–63, 1985; Teware et al. Veterinary Parasitology 62:223–230, 1996). However, the therapeutic benefits obtained using such cell wall extracts to treat cancer cells are variable and inconsistent, and appear to depend on the method by which the preparation is prepared and delivered, and on the stability of the preparation.

Most prior art anti-bladder cancer agents have proven to be less than adequate for clinical applications. Many of these agents are inefficient (Bischoff et al. Science 274:373–376, 1996) or toxic, have significant side effects (Lamm et al. Journal of Urology 153:14444–1450, 1995), result in development of drug resistance or immunosensitization, and are debilitating for the recipient. Moreover, many of these agents depend on Fas, TNFR1 or p53/p21 for their effectiveness.

Therefore, there is a need for a novel therapeutic agent that inhibits proliferation of and induces apoptosis in bladder cancer cells, and that stimulates responsive cells of the immune system to produce bioactive molecules. This therapeutic agent should be useful as an anti-bladder cancer agent and as an adjunct to other anti-bladder cancer agents. By adjunct is meant useful with other anti-bladder cancer agents to increase treatment effectiveness. Moreover, such a therapeutic agent should be simple and relatively inexpensive to prepare, its activity should be reproducible among preparations, its activity should remain stable over time, and its effects on bladder cancer cells should be achievable with dose regimens that are associated with minimal toxicity.

SUMMARY OF THE INVENTION

The mycobacterial cell wall complex (BCC) of the present invention satisfies the above needs by providing a composition comprising a mycobacterial DNA (B-DNA)-mycobacterial cell wall complex (BCC), wherein the B-DNA is preserved and complexed on the mycobacterial cell wall, and a pharmaceutically acceptable carrier, such that the BCC is effective in eliminating cancer cells in the urinary bladder of an animal, including a human. More particularly, the present invention relates to a *Mycobacterium phlei* DNA (M-DNA)-*Mycobacterium phlei* cell wall complex (MCC), wherein the M-DNA is preserved and complexed on the *M. phlei* cell wall, such that the MCC is effective in inhibiting proliferation of and in inducing apoptosis in bladder cancer cells, and in stimulating responsive cells of the immune system to produce bioactive molecules. Methods of making MCC and methods of using MCC also are disclosed.

MCC is simple and relatively inexpensive to prepare, its activity is reproducible among preparations, it remains stable over time, and it is effective at dose regimens that are associated with minimal toxicity.

To prepare MCC, the *Mycobacterium phlei* (*M. phlei*) are grown in liquid medium and harvested. The *M. phlei* are disrupted, and the solid components of the disrupted *M. phlei* are collected by centrifugal sedimentation. The solid components are deproteinized, delipidated, and washed. DNase-free reagents are used to minimize M-DNA degradation during preparation.

MCC, in combination with a pharmaceutically acceptable carrier, is administered to an animal in a dosage sufficient to stimulate to inhibit proliferation of and induce apoptosis in responsive cells of the bladder and to stimulate immune system components, within the bladder, to produce bioactive molecules. MCC can be administered by methods including, but not limited to, suspension in aqueous formulations, emulsification in oil or other hydrophobic liquid formulations, enclosure in liposomes, and complexion with natural or artificial carriers, with tissue- or cell-specific ligands or with tissue- or cell-specific antibodies.

MCC is effective as a therapeutic agent for preventing, treating and eliminating diseases or process mediated by undesired and uncontrolled proliferation of cells including, but not limited to, bladder cancer cells. MCC inhibits proliferation of and induces apoptosis in responsive cancer cells, including, but not limited to, bladder cancer cells, stimulates responsive cells of the immune system including, but not limited to, bladder cancer infiltrating monocytes and macrophages to produce bioactive molecules.

MCC also is effective as an adjunct to enhance the effectiveness of other anti-cancer agents including, but not limited to, anti-bladder cancer agents. Such agents include, but are not limited to, drugs, immunostimulants, antigens, antibodies, vaccines, radiation and chemotherapeutic, genetic, biologically engineered and chemically synthesized agents, and agents that target cell death molecules for activation or inactivation and that inhibit proliferation of and induce apoptosis in responsive cells.

Accordingly it is an object of the present invention to provide a therapeutic composition and method that induces a response in responsive cells of the bladder of an animal, including a human.

Another object of the present invention is to provide a composition and method that is effective to prevent bladder cancer.

Another object of the present invention is to provide a composition and method that is effective to treat bladder cancer.

Another object of the present invention is to provide a composition and method that is effective to eliminate bladder cancer.

Another object of the present invention is to provide a composition and method that inhibits proliferation of bladder cancer cells.

Another object of the present invention to provide a composition and method that induces apoptosis in bladder cancer cells.

Another object of the present invention is to provide a composition and method that induces apoptosis independent of Fas.

Another object of the present invention is to provide a composition and method that induces apoptosis independent of TNFR1.

Another object of the present invention is to provide a composition and method that induces apoptosis independent of p53/p21.

Another object of the present invention is to provide a composition and method that induces apoptosis independent of drug resistance.

Another object of the present invention to provide a composition and method that stimulates responsive cells of the immune system to produce bioactive molecules.

Another object of the present invention is to provide a composition and method that stimulates responsive cells of the immune system to produce reactive oxygen species.

Another object of the present invention is to provide a composition and method that stimulates responsive cells of the immune system to produce cytokines Another object of the present invention is to provide a composition and method that stimulates responsive cells of the immune system to produce IL-6.

Another object of the present invention is to provide a composition and method that stimulates responsive cells of the immune system to produce IL-10.

Another object of the present invention is to provide a composition and method that stimulates responsive cells of the immune system to produce IL-12.

Another object of the present invention is to provide a composition and method that is effective in inhibiting angiogenesis in bladder cancer tumors.

Another object of the present invention is to provide a composition and method that is effective as an adjunct to other anti-bladder cancer therapies.

Another object of the present invention is to provide a composition and method that is effective as an adjunct to chemical anti-cancer agents.

Another object of the present invention is to provide a composition and method that is effective as an adjunct to biological anti-bladder cancer agents.

Another object of the present invention is to provide a composition and method that is effective as an adjunct to biologically engineered anti-bladder cancer agents.

Another object of the present invention is to provide a composition and method that is effective as an adjunct to anti bladder cancer vaccines.

Another object of the present invention is to provide a composition and method that is effective as an adjunct to nucleic acid-based anti-bladder cancer vaccines.

Another object of the present invention is to provide a composition and method that is effective as an adjunct to radiation as an anti-bladder cancer therapy.

Another object of the present invention is to provide a composition of particle size and formulation that is optimal for recognition by responsive cells.

Another object of the present invention is to provide a composition of particle size and formulation that is optimal for interaction with responsive cells.

Another object of the present invention is to provide a composition of particle size and formulation that is optimal for uptake by responsive cells.

Another object of the present invention is to provide a composition that can be prepared in large amounts.

Another object of the present invention is to provide a composition that is relatively inexpensive to prepare.

Another object of the present invention is to provide a composition that has reproducible activity among preparations.

Another object of the present invention is to provide a composition that remains stable over time.

Another object of the present invention is to provide a composition that maintains its effectiveness over time.

Another object of the present invention is to provide a composition that is minimally toxic to the recipient.

Another object of the present invention is to provide a composition that will not cause anaphylaxis in the recipient.

These and other objects, features and advantages of the present invention will become apparent after a review of the following detailed description of the disclosed embodiment and the appended claims.

DETAILED DESCRIPTION OF THE INVENTION

Figure 1:
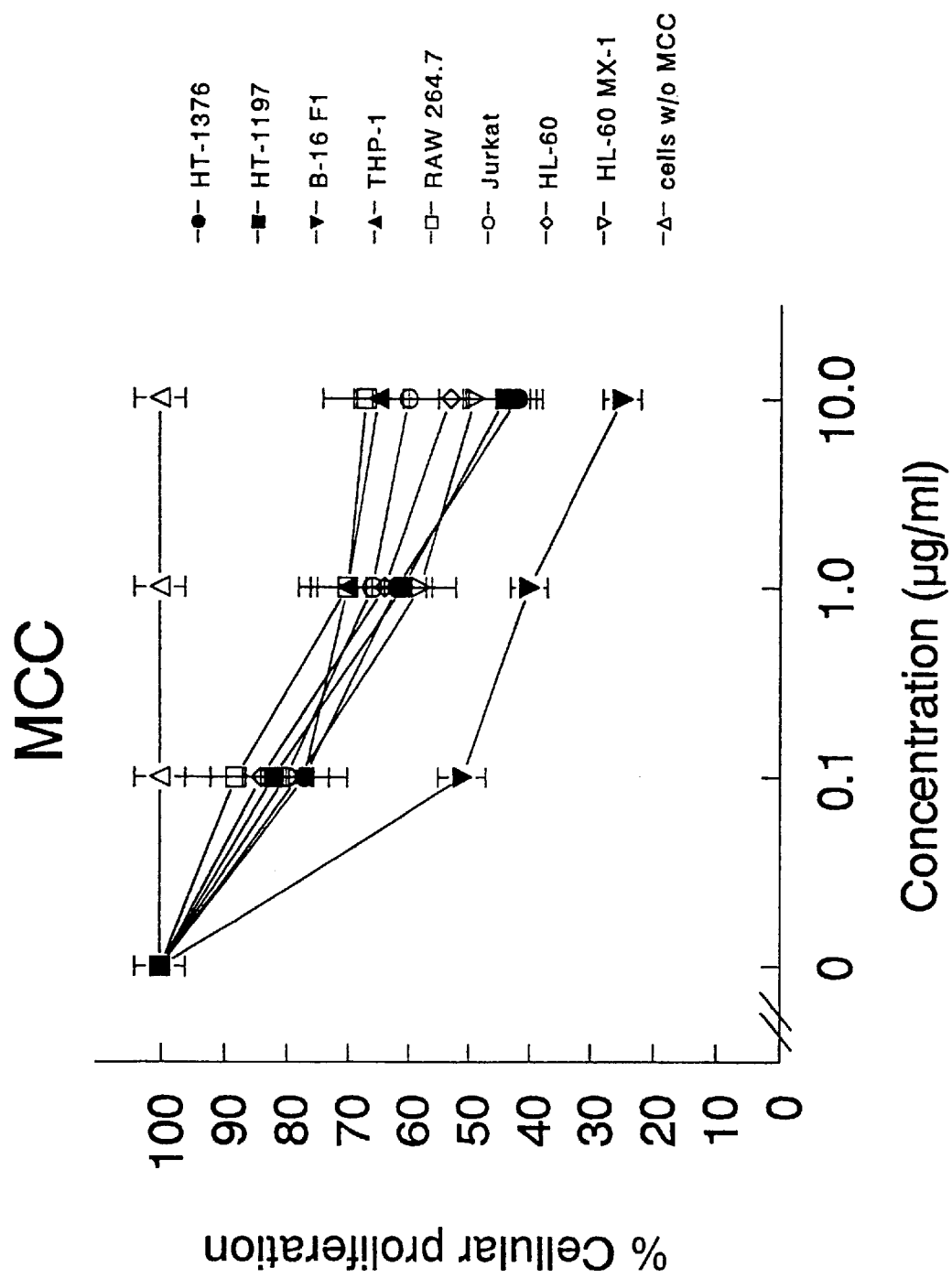
FIG. 1. Inhibition of proliferation of HT-1376. HT-1197, B-16 F1, THP-1, RAW 264.7, Jurkat, HL-60 and HL-60 MX-1 cancer cells by MCC. Results are the mean±SD of 3 independent experiments.

The present invention relates to a therapeutic composition comprising a mycobacterial deoxyribonucleic acid (B-DNA)-mycobacterial cell wall-complex (BCC), wherein the B-DNA is preserved and complexed on the mycobacterial cell wall, such that the BCC is effective in inducing a response in responsive cells of an animal, including a human. More particularly, the present invention relates to a *Mycobacterium phlei* (*M. phlei*) deoxyribonucleic acid (M-DNA)-*M. phlei* cell wall-complex (MCC), wherein the M-DNA is preserved and complexed on the *M. phlei* cell wall, such that the MCC is effective in inducing a response in responsive cells in the urinary bladder of an animal effective to eliminate cancer cells in the urinary bladder of the animal. In MCC, the amount of M-DNA is enriched relative to the amount of M-DNA in an intact *M. phlei* cell. Further, the M-DNA is preserved and is complexed on the *M. phlei* cell wall so that it is more accessible to the responding cells than is the M-DNA within an intact *M. phlei* cell.

Many bacterial species can be used to practice the present invention including, but not limited to, Coryneform species, Corynebacterium species, Rhodococcus species, Eubacterium species, Bordetella species, Escherichia species, Listeria species, Nocardia species and Mycobacterium species. Preferably, BCC is prepared from a Mycobacterium species including, but not limited to, *M. smegmatis, M. fortuitum, M. kansaii, M. tuberculosis, M. bovis, M. vaccae, M. avium* and *M. phlei,* Most preferably, MCC is prepared from the Mycobacterium species *M. phlei.*

MCC is simple and relatively inexpensive to prepare, its activity is reproducible among preparations, it remains stable over time, and maintains its therapeutic effectiveness over time. MCC is effective at dose regimens that are minimally, if at all toxic to the recipient, does not cause a positive tuberculin reaction in the recipient and rarely causes an anaphylactic response in the recipient, even upon repeated administration.

The therapeutically active ingredients of MCC include, but are not limited to, M-DNA and the deproteinized, delipidated cell wall of the *M. phlei* on which the M-DNA is complexed. Although not wanting to be bound by the following hypothesis, it is believed that M-DNA, in the form of short oligonucleotides, and its physical association with *M. phlei* cell wall both contribute to optimal expression of MCC's therapeutic activity. This activity includes, but is not limited to, inhibition of proliferation of cancer cells including, but not limited to, bladder cancer cells; induction of apoptosis in cancer cells including, but not limited to, bladder cancer cells; and, stimulation of responsive cells of the immune system including, but not limited to, bladder cancer infiltrating monocytes and macrophages.

The M-DNA content of MCC preferably is between about 0.001 mg/100 mg dry MCC and about 90 mg/100 mg dry MCC, more preferably between about 0.01 mg/100 mg dry MCC and about 40 mg/100 mg dry MCC, most preferably between about 0.1 mg/100 mg dry MCC and about 30 mg/100 mg dry MCC. Also, it is preferable that the protein content be less than about 2 mg/100 mg dry MCC and that the fatty acid content be less than about 2 mg/100 mg dry MCC.

Methods to increase the therapeutic activity of MCC include, but are not limited to, chemically supplementing or biotechnologically amplifying stimulatory sequences or confirmations of DNA derived from the same or different bacterial species, or using bacterial plasmids containing appropriate stimulatory sequences or confirmations of DNA derived from the same or different bacterial species. Other methods to increase the therapeutic activity of MCC include, but are not limited to, complexing the MCC to natural or synthetic carriers or coupling the MCC to tissue-type or cell-type directed ligands or antibodies.

Administration of MCC is not an immunization process, but is a therapeutic treatment that inhibits proliferation of and induces apoptosis in responsive cells, and that stimulates responsive cells of the immune system to produce bioactive molecules. Moreover, the unexpected and surprising ability of MCC to inhibit proliferation of and to induce apoptosis in bladder cancer cells lines including, but not limited to, HT-1376 human bladder cancer cells, which are p52/21 abnormal and drug resistant, addresses a long felt unfulfilled need in the medical arts, and provides an important benefit for animals, including humans.

Although not wanting to be bound by the following hypothesis, it is believed that the therapeutic activities of MCC include, but are not limited to, induction of caspase activity resulting in apoptosis and stimulation of the immune system to produce bioactive molecule resulting in apoptosis and in cytolysis. Apoptosis and cytolysis, individually and in combination, have both anti-cancer activity and adjunct activity. That is, MCC alone can be used as an anti-bladder cancer agent and MCC can be used before, at the same time as, or after another anti-bladder cancer agent to increase treatment effectiveness.

MCC and its pharmaceutically acceptable carrier may be prepared by various techniques. Such techniques include the step of bringing into association the MCC and its carriers. Preferably, the compositions are prepared by uniformly and intimately bringing into association the MCC with liquid carriers, with solid carriers, or with both. Liquid carriers include, but are not limited to, aqueous compositions, non-aqueous compositions or both. Solid carriers include, but are not limited to, biological carriers, chemical carriers or both.

MCC may be administered in an aqueous suspension, oil emulsion, water in oil emulsion and water-in-oil-in-water emulsion and in carriers including, but not limited to, liposomes, microparticles, site-specific emulsions, long-residence emulsions, sticky-emulsions, microemulsions, nanoemulsions, microspheres, nanospheres, nanoparticles and minipumps, and with various natural or synthetic polymers that allow for sustained release of MCC, the minipumps or polymers being implanted in the vicinity of where drug delivery is required. Polymers and their use are described in, for example, Brem et al. (Journal of Neurosurgery 74:441–446, 1991). Further, MCC can be used with any one, all, or any combination of excipients regardless of the carrier used to present MCC to the responding cells. These include, but are not limited to, anti-oxidants, buffers, and bacteriostats, and may include suspending agents and thickening agents.

Preferably, MCC is administered as an aqueous suspension. For administration in an aqueous carrier, MCC is suspended in a pharmaceutically acceptable buffer including, but not limited to, saline and phosphate buffered saline (PBS) by techniques including, but not limited to, sonication and microfluidization and is either asceptically processed or terminally sterilized. For example, freeze-dried (lyophilized) MCC may be stored in sealed ampoules or vials requiring only the addition of a carrier, for example sterile water, immediately prior to use.

For administration in a non-aqueous carrier, MCC is emulsified with a mineral oil or with a neutral oil such as, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, soybean oil, canola oil, palm oil, olive oil and myglyol, wherein the number of fatty acid carbons is between 12 and 22 and wherein the fatty acids can be saturated or unsaturated. Optionally, charged lipid or phospholipid can be suspended in the neutral oil.

The size of the MCC particles should be optimal for recognition of, interaction with, and uptake by the responsive cells. Preferably, the mean diameter of the MCC particles is between about 10 and about 10,000 nm, more preferably between about 100 and about 1000 nm and most preferably between about 250 and about 600 nm.

MCC is administered in an amount effective to induce a therapeutic response in responsive cells of the bladder. The dosage of MCC to be administered will depend on the condition being treated, the particular formulation, and other clinical factors such as weight and condition of the recipient and route of administration. Preferably, the amount of MCC administered is from about 0.00001 mg/kg to about 100 mg/kg per dose, more preferably from about 0.0001 mg/kg to about 50 mg/kg per dose, and most preferably from about 0.001 mg/kg to about 10 mg/kg per dose.

M-DNA also may administered in an amount effective to induce a therapeutic response in responsive cells of the bladder. The dosage of M-DNA to be administered will depend on the condition being treated, the particular formulation, and other clinical factors such as weight and condition of the recipient and route of administration. Preferably the amount of M-DNA administered is from about 0.00001 mg/kg to about 100 mg/kg per dose, more preferably from about 0.0001 mg/kg to about 50 mg/kg per dose and most preferably from about 0.001 mg/kg to about 10 mg/kg per dose.

Routes of administration include, but are not limited to, oral, topical, subcutaneous, intramuscular, intraperitoneal, intravenous, intradermal, intrathecal, intralesional, intratumoral, intrabladder, intra-vaginal, intraocular, intrarectal, intrapulmonary, intraspinal, transdermal, subdermal, placement within cavities of the body, nasal inhalation, pulmonary inhalation, impression into skin and electrocorporation. Preferably, MCC is administered by instillation into the urinary bladder by, but not limited to, a urinary tract catheter. Other methods for instilling MCC into the urinary bladder are known to those skilled in the art.

Depending on the route of administration, the volume per dose is preferably about 0.001 ml to about 100 ml, more preferably about 0.01 ml to about 50 ml, and most preferably about 0.1 ml to about 30 ml. MCC can be administered in a single dose treatment or in multiple dose treatments on a schedule and over a period of time appropriate to the disease being treated, the condition of the recipient and the route of administration.

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Preparation of MCC from *Mycobacterium phlei*

MCC was prepared from *Mycobacterium phlei* (strain 110). *M. phlei* was obtained from the Institut fur Experimental Biologie and Medizin, Borstel, Germany, and was stored as a suspension in sterile milk at −60° C. The *M. phlei* was cultured on Petragnani medium (Difco Labs, Detroit, Mich.) and was grown in granulated agar BACTO® AC broth (Difco Labs) for 10 to 20 days. The cells were harvested by centrifugal sedimentation. All reagents used in the following procedure were selected to enhance conservation of the *M. phlei* DNA.

About 400 grams of moist cell mass was placed into an autoclaved blender with a capacity of about 1200 ml. The cell mass was mixed at high speed for between 30 to 60 sec. After mixing, 6 ml of DNase-free 80% polyoxethylenesorbitan monooleate TWEEN 80 (Sigma Chemical Co., St. Louis, Mo.) and between 200 and 400 ml of autoclaved water were added to the cell mixture. The entire cell suspension was again mixed in the blender at low speed for about 10 sec.

Cell disruption was accomplished by sonication. Five hundred ml of cell suspension, wherein the cells comprised about 50% to 70% of the volume, were placed in a one liter autoclaved beaker and sonicated. The sonicate was stored in an autoclaved flask on ice during the fractionation process. Unbroken cells were remove by low speed centrifugation. The supernatant from the low speed centrifugation was centrifuged for 1 h at 27,500 g at 15° C. and the supernatant from this centrifugation was discarded.

The sediment from the 27,000 g centrifugation was transferred to an autoclaved blender and suspended in autoclaved deionized water by mixing at low speed. This suspension was again centrifuged at 27,000 g at 15° C. for 1 h and the supernatant was again discarded. The sediment was suspended in autoclaved deionized water and spun for 5 min at 350 g to sediment any remaining unbroken cells. The supernatant was decanted and centrifuged at 27,000 g for 1 h at 15° C. to sediment the crude cell wall fraction.

The crude cell wall fraction was deproteinized by digestion with proteolytic enzymes, care being taken to use DNase-free reagents where possible to optimize the amount of M-DNA in the preparation and to preserve the structure of the M-DNA in the preparation. The crude cell wall fraction derived from about 400 g of whole cells was suspended in 1 liter of 0.05 M DNase-free Tris-HCl, pH 7.5, by mixing at low speed. After the crude cell wall fraction was thoroughly suspended, 50 mg of DNase-free trypsin (Sigma Chemical Co) was added and the suspension was stirred using a magnetic stirring bar at 35° C. for 6 h. Following trypsin treatment, 50 mg of DNase-free pronase (Amersham Canada Limited, Oakville, Ontario) were added to each liter of trypsin-treated crude cell wall suspension. The suspension was stirred using a magnetic stirring bar for 12 to 18 h at 35° C.

After proteolytic digestion, the crude cell wall fraction was delipidated with detergent and phenol. To each liter of suspension, 60 g of DNase-free urea (Sigma Chemical Co.), 2.0 ml of DNase-free 100% phenol or 150 ml of 90% w/v phenol (Sigma Chemical Co.) were added. The flask containing the suspension was covered loosely with aluminum foil, warmed to 60°–80° C. and stirred for 1 hr. The suspension was spun for 10 min at 16,000 g. The supernatant fraction and the fluid beneath the pellet were discarded. The pellet was washed 3 times by resuspension in about 1 liter of autoclaved deionized water and centrifuged for 10 min at 16,000 g.

The washed, deproteinized, delipidated MCC was lyophilized by transferring the suspension to an autoclaved lyophilizing flask with a small amount of autoclaved water. One 300 ml lyophilizing flask was used for each 30 grams of wet cell complex starting material. The MCC suspension was shell frozen by rotating the flask in ethanol cooled with solid carbon dioxide. After the content of the flask was frozen, the flask was attached to a lyophilization apparatus (Virtis Co. Inc., Gardiner, N.Y.) and lyophilized. After lyophilization, the sample was transferred to an autoclaved screw-cap container and stored at –20° C. in a desiccator jar containing anhydrous calcium sulfate.

Unless stated otherwise, the lyophilized MCC was resuspended in autoclaved deionized water or in a pharmaceutically acceptable DNase-free buffer such as, but not limited to, saline and PBS, and emulsified by sonication. Optionally, the MCC suspension was homogenized by microfluidization at 15,000–30,000 psi for one flow-through. The MCC suspension was either processed under aseptic conditions or was sterilized by autoclaving.

EXAMPLE 2
Purification of M-DNA from MCC and from *M. phlei*

MCC was prepared as in Example 1. M-DNA was purified from MCC (MCC-DNA) by phenol/chloroform/isoamyl alcohol extraction and ethanol precipitation (Short Protocols in Molecular Biology, 3rd Edition, Ausubel et al. Eds., John Wiley & Sons Inc., New York, USA). Unexpectedly, we found that at least about 3.6% of the dry weight of MCC is extractable M-DNA.

M-DNA was purified from *M. phlei* (*M. phlei*-DNA) by suspending the *M. phlei* (strain 110) in 5 ml of DNase-free 50 mM Tris-HCl, 5 mM EDTA, pH 8.0, adding DNase-free lysozyme (Sigma Chemical Co.) to a concentration of 1 mg/ml and incubating for 90 min at 37° C. DNase-free Proteinase K (Life Technologies, Burlington, Ontario, Canada) was added to a concentration of 0.1 mg/ml, DNase-free sodium dodecyl sulfate (BioRad, Richmond, Calif.) was added to a concentration of 1% and the incubation was continued for 10 min at 65° C. The M-DNA (MCC-DNA or *M. phlei*-DNA) was phenol/chloroform/isoamyl alcohol extracted and ethanol precipitated.

Unless stated otherwise, the M-DNA was sonicated in autoclaved deionized water or in a DNase-free pharmaceutically acceptable buffer such as, but not limited to, saline and PBS. MCC, MCC-DNA and *M. phlei*-DNA do not contain endotoxins as determined using a Limulus amebocyte lysate QCL-1000 kit (BioWhittaker, Walkersville, Md.).

EXAMPLE 3
Preparation of Bacterial-DNA-bacterial Cell Wall Complex and of Bacterial DNA from Other Bacterial Species Bacterial DNA-bacterial cell wall complex is prepared from *M. smegmatis, M. fortuitous, Nocardia rubra, Nocardia asteroides, Cornybacterium parvum, M. kansaii, M tuberculosis* and *M. bovis* as in Example 1. Bacterial-DNA is purified from bacterial DNA-bacterial cell wall complex and from intact bacteria as in Example 2.

EXAMPLE 4
DNase Treatment

MCC-DNA, *M-phlei*-DNA and MCC, each containing 1 µg of M-DNA, and REGESSIN® (U.S. Pat. No. 4,744,984) were digested with 1 international unit (IU) of RNase-free DNase I (Life Technologies) for 1 h at 25° C. in 20 mM Tris HCl, pH 8.4, 2 mM MgCl$_2$ and 50 mM KCl. DNase I was inactivated by the addition of EDTA to a final concentration of 2.5 mM and heating for 10 min at 65° C. DNase I digests both single stranded and double stranded DNA. Digestion with DNase I results in almost total degradation of DNA. Regressin® (Bioniche, Inc. London, Ontario, Canada) is a formulation containing 1 mg mycobacterial cell wall extract, 20 µl mineral oil NF in 1 ml PBS and 0.5% v/v of Tween 80.

EXAMPLE 5
Cells and Reagents

All cell lines, except OC2 and SW260, were obtained from the American Type Culture Collection (ATCC, Rockville, Md.) and were cultured in the medium recommended by the ATCC. OC2 and SW260 were obtained from Dr. J. K. Collins (University College Cork, Cork, Ireland) and were cultured in DMEM medium supplemented with 10% FCS. Table 1 shows the cell lines, their origins and their properties.

TABLE 1

| Cell lines | | |
|---|---|---|
| CELL LINE | ORIGIN | PROPERTIES |
| THP-1 | Human acute monocytic leukemia | |
| HL-60 | Human promyelocytic leukemia | |
| HL-60 MX-1 | Human promyelocytic leukemia | Atypical drug resistance to mixoxantrone |
| RAW 264.7 | Murine monocytic leukemia | |
| JURKAT | Human T lymphoblast | |
| HT-1376 | Human bladder carcinoma | Mutation in p53/p21 MDR |
| HT-1197 | Human bladder carcinoma | |
| B-16-F1 | Murine melanoma | |
| SW260 | Human colon adenocarcinoma | FAS-L resistance |
| OC2 | Human esophageal carcinoma | |
| LS1034 | Human cecum carcinoma | Conventional MDR |

HT-1197 are anaplastic transitional bladder carcinoma grade 4 cells developed from a human male. HT-1197 cells are sensitive to chemotherapeutic agents such as, but not limited to, doxorubicin. HT-1376 are anaplastic transitional bladder carcinoma grade 3 cells developed from a human female. HT-1376 cells are p53/p21 abnormal and are resistant to chemotherapeutic agents such as, but not limited to, cisplatin and mitomycin. HT-1197 cells and HT-1376 cells were grown in MEM supplemented with non-essential amino acids and vitamins and containing 10% FCS (MEM-FCS) (Gibco Life Science).

Murine macrophages were obtained from female CD1 mice injected intra-peritoneally with 1.5 ml sterile Brewer's thioglycolate broth (Difco, Detroit, Md.). The peritoneal exudate (>85% macrophages) was harvested at day 4, washed by centrifugation in HBSS and cultured in RPMI-1640 medium supplemented with 10% FCS, 2 mM L-glutamine and 20 mM HEPES (Gibco Life Science). The cells were allowed to adhere for 18 h after which non-adherent cells were removed by gentle washing with warm medium.

Murine spleen cells were prepared by gentle teasing through sterile stainless steel screens. Cell suspensions were layered on Lympholyte-M cell separation media (CedarLane, Hornby, Ontario, Canada) and centrifuged at 2200 rpm for 30 min to remove red blood cells and dead cells. These cells were cultured in RPMI-1640 medium supplemented with 10% FCS, 2 mM L-glutamine and 20 mM HEPES (Gibco Life Science).

Unless stated otherwise, cells were seeded in 6 well flat-bottom tissue culture plates at concentrations between $3 \times 10^5$ and $10^6$ cells/ml and were maintained at 37° C. in a 5% CO2 atmosphere.

Calf thymus-DNA, herring sperm-DNA and *Escherichia coli* lipopolysaccharide (LPS) were obtained from Sigma Chemical Co. Recombinant human IL-12 (hIL-12) was obtained from R&D Systems (Minneapolis, Minn.).

EXAMPLE 6
Inhibition of Cell Proliferation

Cell proliferation was determined using dimethylthiazol-diphenyltetrazolium bromide (MTT) reduction (Mosman et al. Journal of Immunological Methods 65:55–63, 1983).

HT-1376, HT-1197, B-16 F1, THP-1, RAW 264.7, Jurkat, HL-60 and HL-60 MX-1 cells were incubated for 24 h with from 0 μg/ml to 10 μ/ml of MCC. MCC inhibited proliferation in each of the cancer cell lines tested in a dose dependent manner (FIG. 1).

Figure 2A:
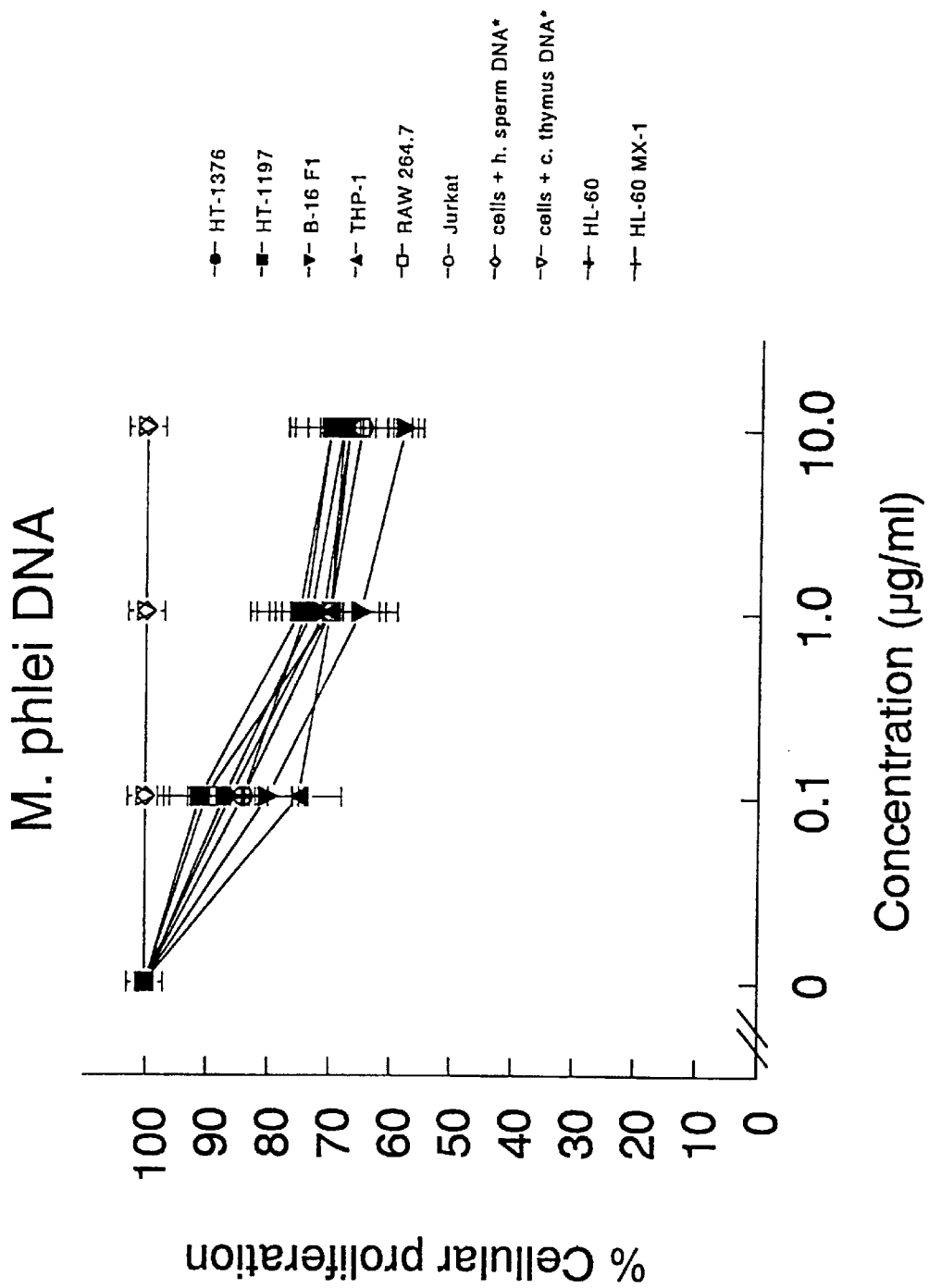
FIGS. 2A and 2B. Inhibition of proliferation of HT-1376, HT-1197, B-16 F1, THP-1, RAW 264.7, Jurkat, HL-60, HL-60 MX-1 cancer cells by *M. phlei*-DNA (2A), MCC-DNA (2B), calf thymus-DNA (2A & 2B) and herring sperm-DNA (2A & 2B). Results are the mean±SD of 3 independent experiments.
Figure 2B:
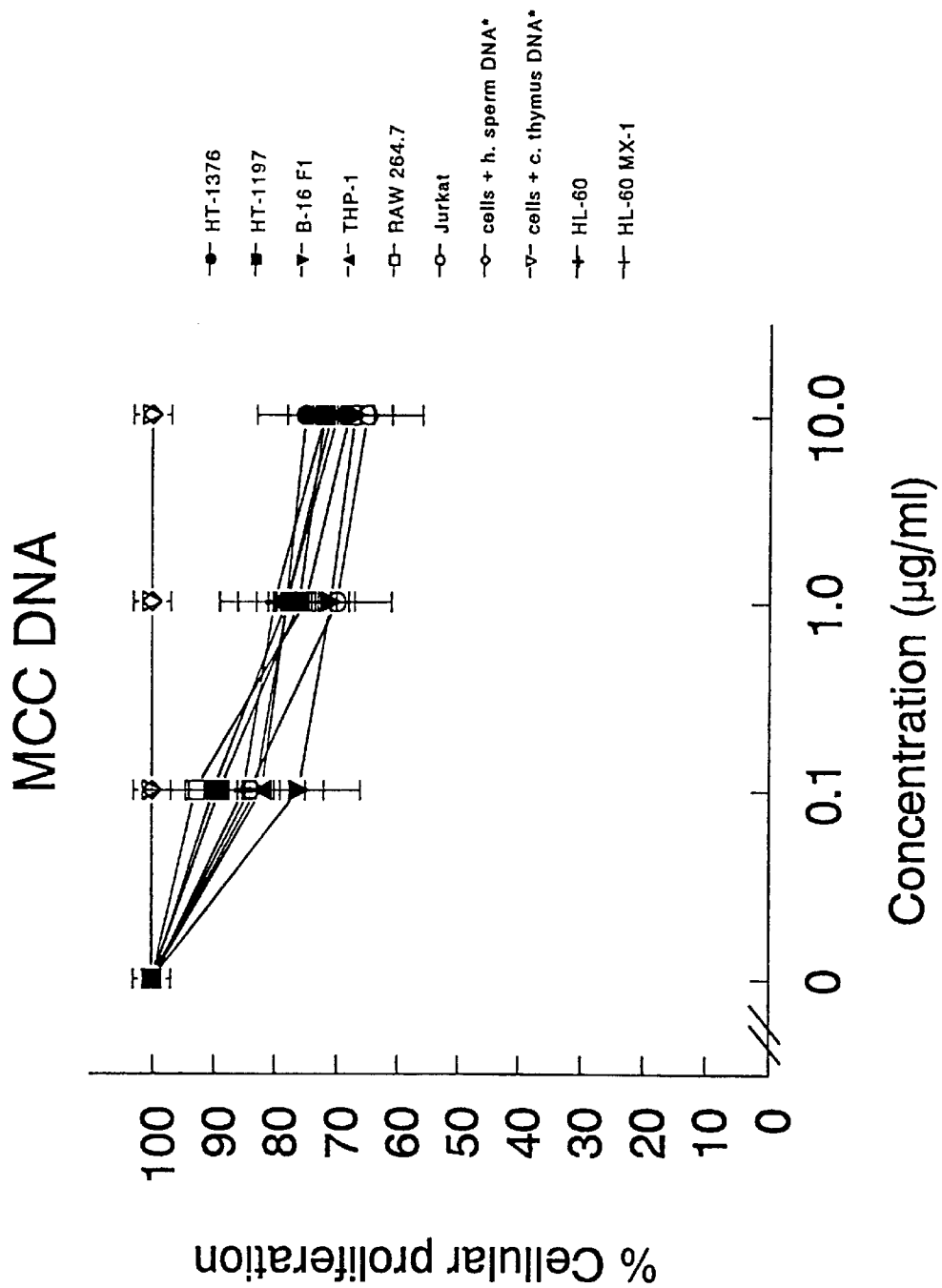

HT-1376, HT-1197, B-16 F1, THP-1, RAW 264.7, Jurkat, HL-60 and HL-60 MX-1 cells were incubated for 24 h with from 0 μg/ml to 10 μg/ml of *M. phlei*-DNA, MCC-DNA, herring sperm-DNA and calf thymus-DNA. *M. phlei*-DNA (FIG. 2A) and MCC-DNA (FIG. 2B) inhibited proliferation in each of the cell lines tested in a dose-dependent manner, whereas herring sperm-DNA (FIGS. 2A & 2B) and calf thymus-DNA (FIGS. 2A & 2B) did not inhibit proliferation of any of the cell lines tested.

Figure 3A:
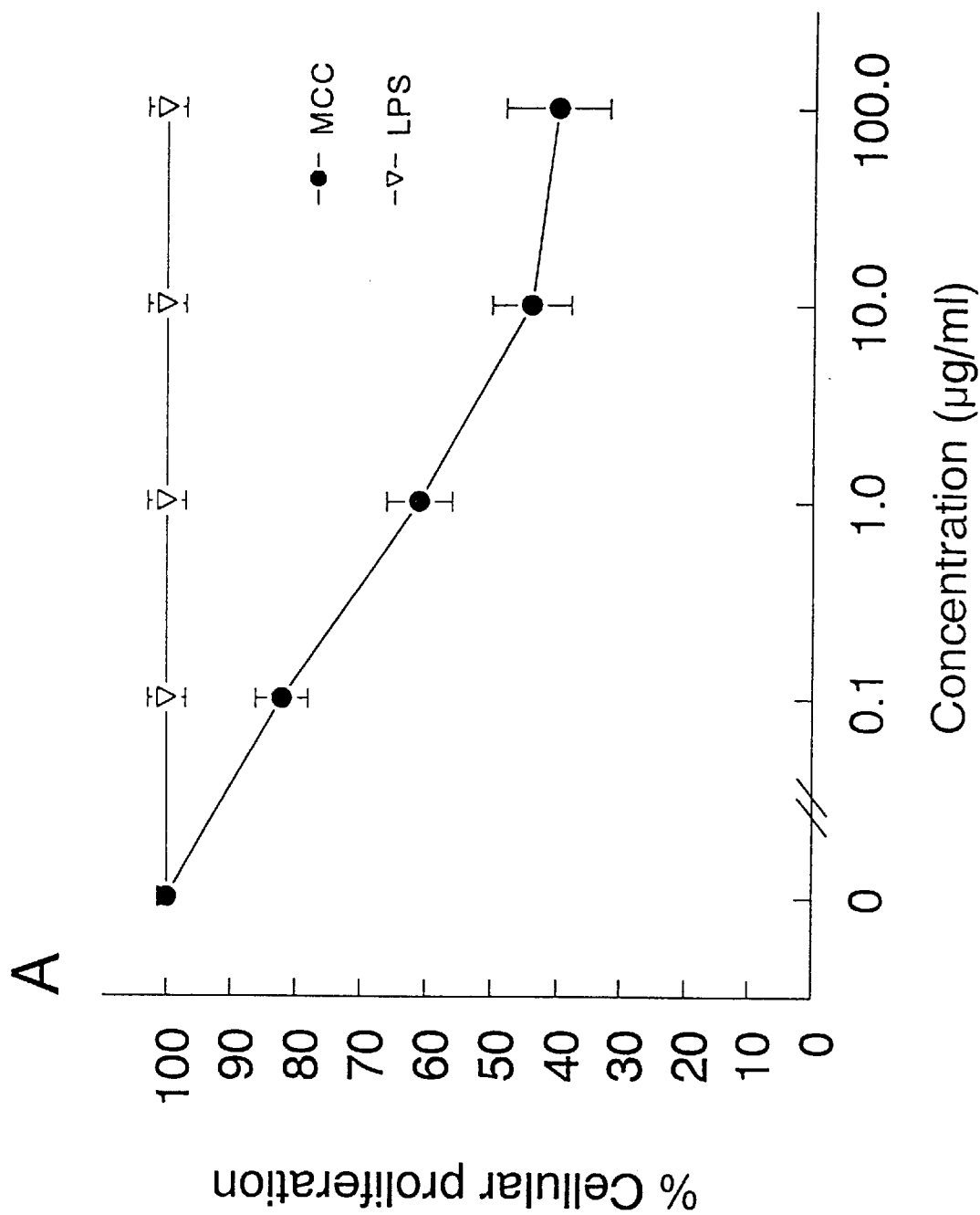
FIGS. 3A and 3B. Inhibition of proliferation of HT-1197 (3A) and HT-1376 (3B) human bladder cancer cells by MCC and LPS. Results are the mean±SD of 3 independent experiments.
Figure 3B:
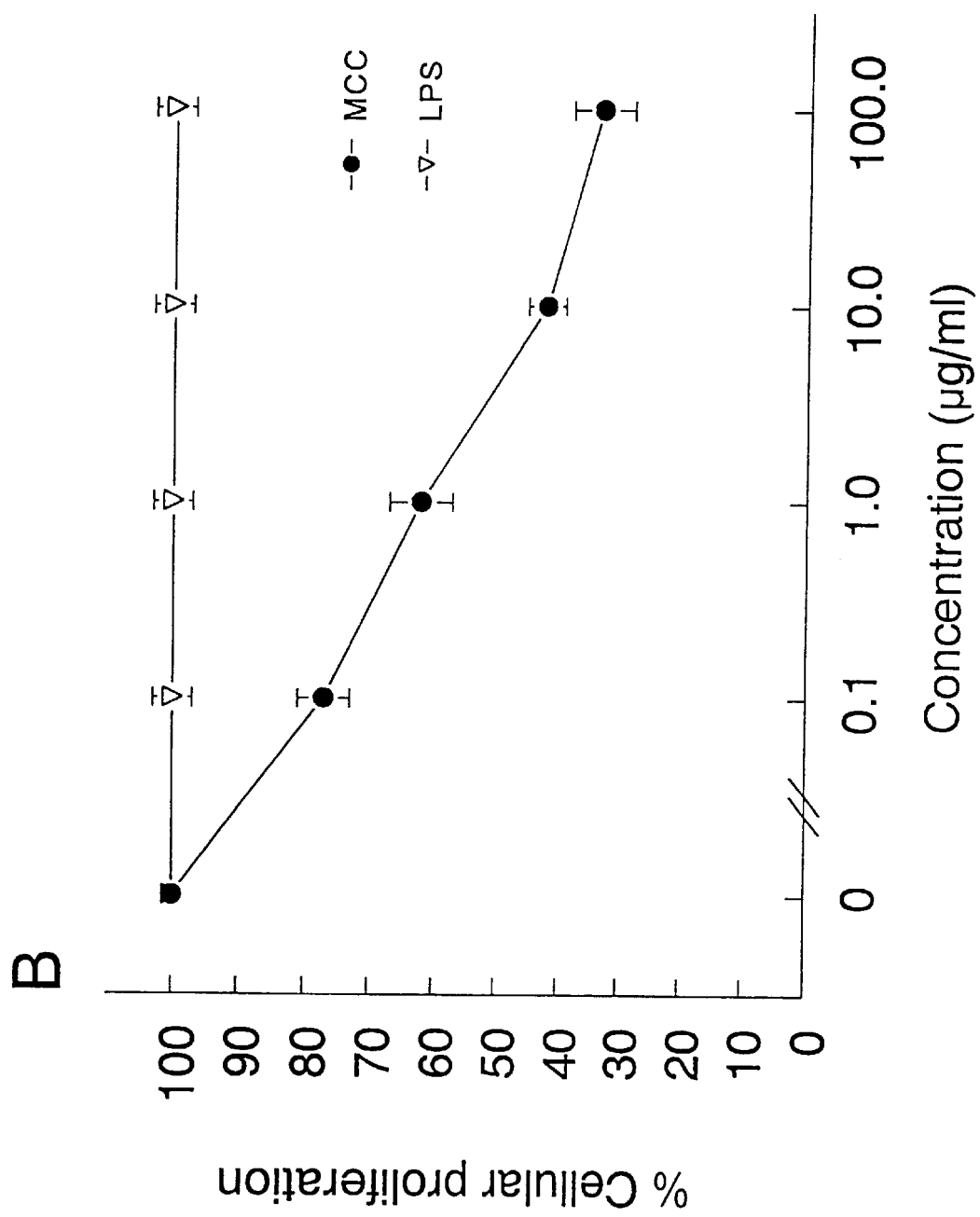

HT-1197 and HT-1376 human bladder cancer cells were incubated for 24 h with from 0 to 100 μ/ml of MCC and LPS. MCC inhibited proliferation in a dose dependent manner in both HT-1197 (FIG. 3A) and HT-1376 (FIG. 3B), whereas LPS did not inhibit proliferation in either of the human bladder cancer cells lines.

MCC, *M. phlei*-DNA and MCC-DNA inhibit proliferation of cancer cells in a dose dependent manner. In contrast LPS, which is a nonspecific immunostimulant and is reported to inhibit proliferation in some cancer cell lines (Izquierdo et al. Anticancer Drugs 7:275–2801996); hIL-12, which is a cytokine, and is reported to inhibit proliferation in some cancer cell lines (Stine et al. Annals NY Academy of Science 795:420–421, 1996); and, DNA from herring sperm and calf thymus do not inhibit proliferation of any of the cancer cells.

These data demonstrate that M-DNA and MCC, wherein M-DNA is preserved and complexed on *M. phlei* cell wall, inhibit proliferation of cancer cells, including HT-1197 human bladder cancer cells, p53/p21 abnormal and drug resistant HT-1376 human bladder cancer cells, and atypical drug resistant HL-60 MX-1 human promyelocytic leukemia cells. Moreover, these data demonstrate M-DNA inhibition of cell proliferation is not common to all DNAs (herring sperm-DNA and calf thymus-DNA) and does not result from nonspecific immunostimulation (LPS) or from cytokine activity (hIL-12).

EXAMPLE 7
Induction of Apoptosis as Indicated by DNA Fragmentation

Fragmentation of cellular DNA into nucleosome-sized fragments is characteristic of cells undergoing apoptosis. Nucleosome-sized fragments are DNA fragments possessing a difference of about 200 base-pairs in length as determined by agarose gel electrophoresis (Newell et al. Nature 357:286–289, 1990). To assess DNA fragmentation, non-adherent cells were collected by centrifugation at 200 g for 10 min. Pellets of non-adherent cells and the remaining adherent cells were lysed with 0.5 ml of hypotonic lysing buffer (10 mM Tris buffer, 1 mM EDTA, 0.2% Triton X-100, pH 7.5). The lysates were centrifuged at 13,000 g for 10 min and the supernatants, containing fragmented DNA, were precipitated overnight at −20° C. in 50% isopropanol and 0.5 M NaCl. The precipitates were collected by centrifugation and were analyzed by electrophoresis in 0.7% agarose gels for 3 h at 100V.

Figure 4A:
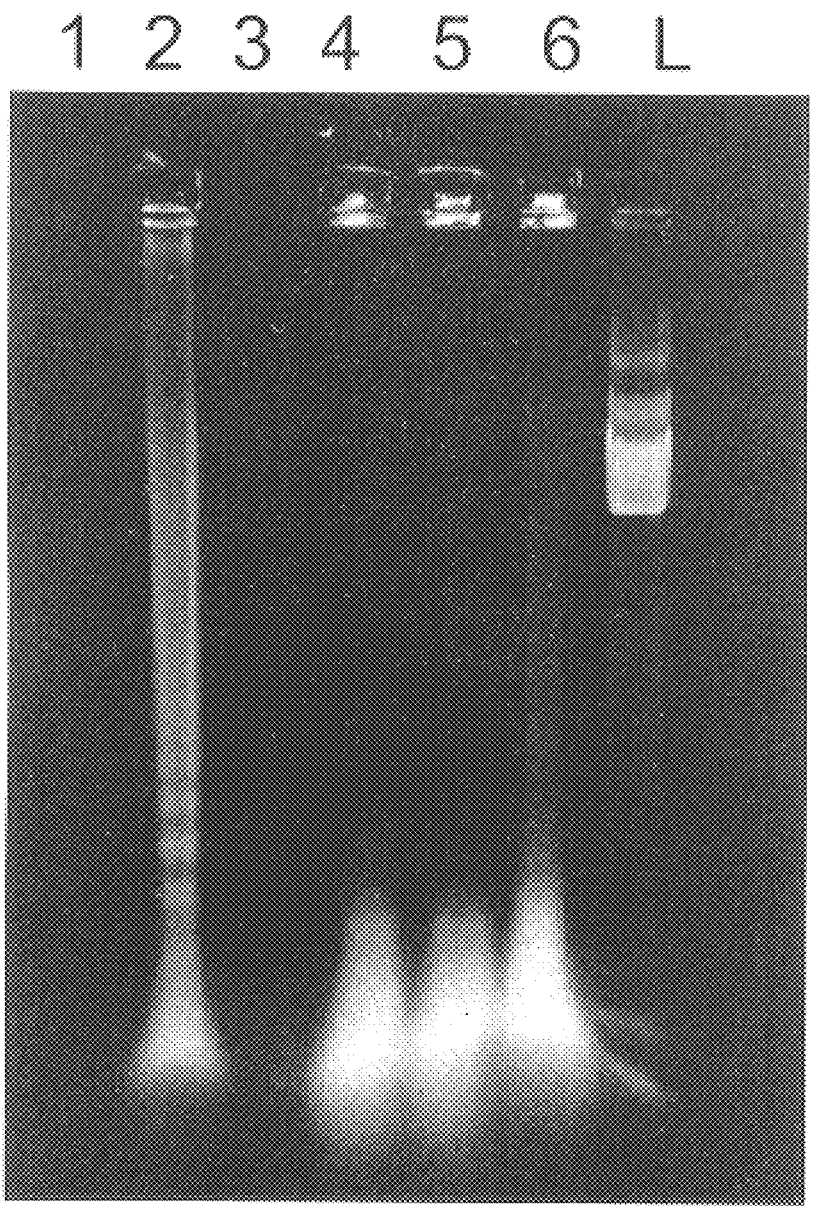
FIGS. 4A and 4B. Induction of DNA fragmentation in HT-1197 (4A) and HT-1376 (4B) human bladder cancer cells by untreated and DNase I treated MCC and by hIL-12. Results shown are for 1 of 3 experiments, each of which gave similar results.
Figure 4B:
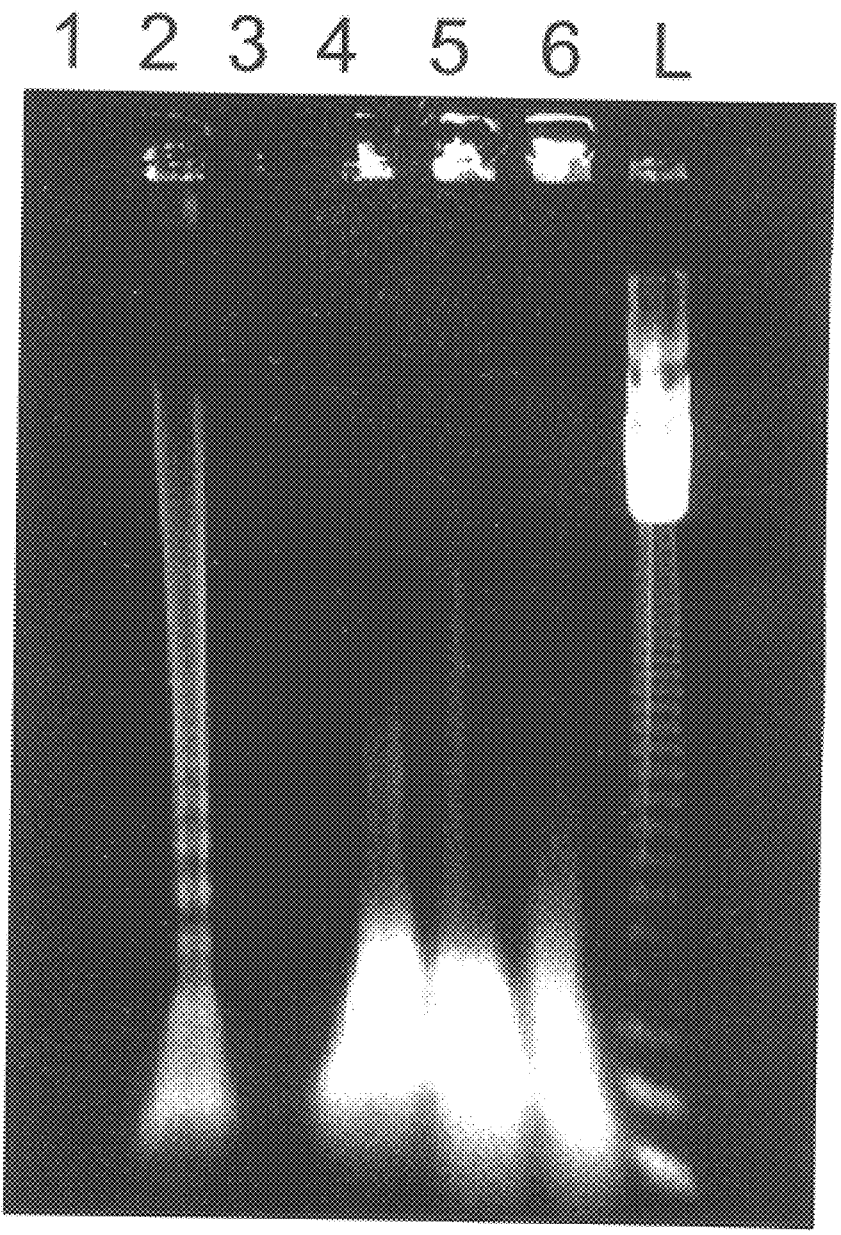

HT-1197 and HT-1376 human bladder cancer cells were incubated for 48 h with 1 μ/ml MCC or with 1 ng/ml hIL-12. MCC induced significant DNA fragmentation in non-adherent HT-1197 (FIG. 4A, lane 2) and HT-1376 (FIG. 4B, lane 2) cells, but not in adherent HT-1197 (FIG. 4A, lane 3) and HT-1376 (FIG. 4B, lane 3) cells. PBS (FIGS. 4A & 4B, lane 5), hIL-12 (FIGS. 4A & 4B, lane 4), DNase I-treated MCC (FIGS. 4A & 4B, lane 7) did not induce DNA fragmentation in non-adherent HT-1197 or HT-1376 cells. Untreated cells (FIGS. 4A & 4B, lane 1) showed no DNA fragmentation. A 123-bp DNA ladder (Gibco Life Science) was used to determine the molecular weight of the nucleosome-sized DNA fragments (FIGS. 4A & 4B, lane L).

As indicated by DNA fragmentation, MCC, wherein M-DNA is preserved and complexed on *M. phlei* cell wall, induces apoptosis in HT-1197 and HT-1376 human bladder cancer cells, whereas DNase I treated MCC does not induce apoptosis in these cells. These data suggest that the intact oligonucleotide structure of the M-DNA is necessary for apoptosis induction in bladder cancer cells. Again, IL-12, which is reported to induce apoptosis in some bladder cancer cells (Stine et al. Annals NY Academy of Science 795:420–421, 1996), does not induce apoptosis in HT-1197 and HT-1376 bladder cancer cells.

EXAMPLE 8
Induction of Apoptosis as Indicated by Solubilization of Nuclear Mitotic Protein Apparatus (NuMA)

Striking morphological changes in the cell nucleus caused by the solubilization and release of NuMA are characteristic of apoptosis. The release of NuMA from the cultured cells was determined in units/ml (U/ml) using a commercial ELISA (Calbiochem, Cambridge, Mass.) (Miller et al. Biotechniques 15:1042–1047, 1993).

Figure 5:
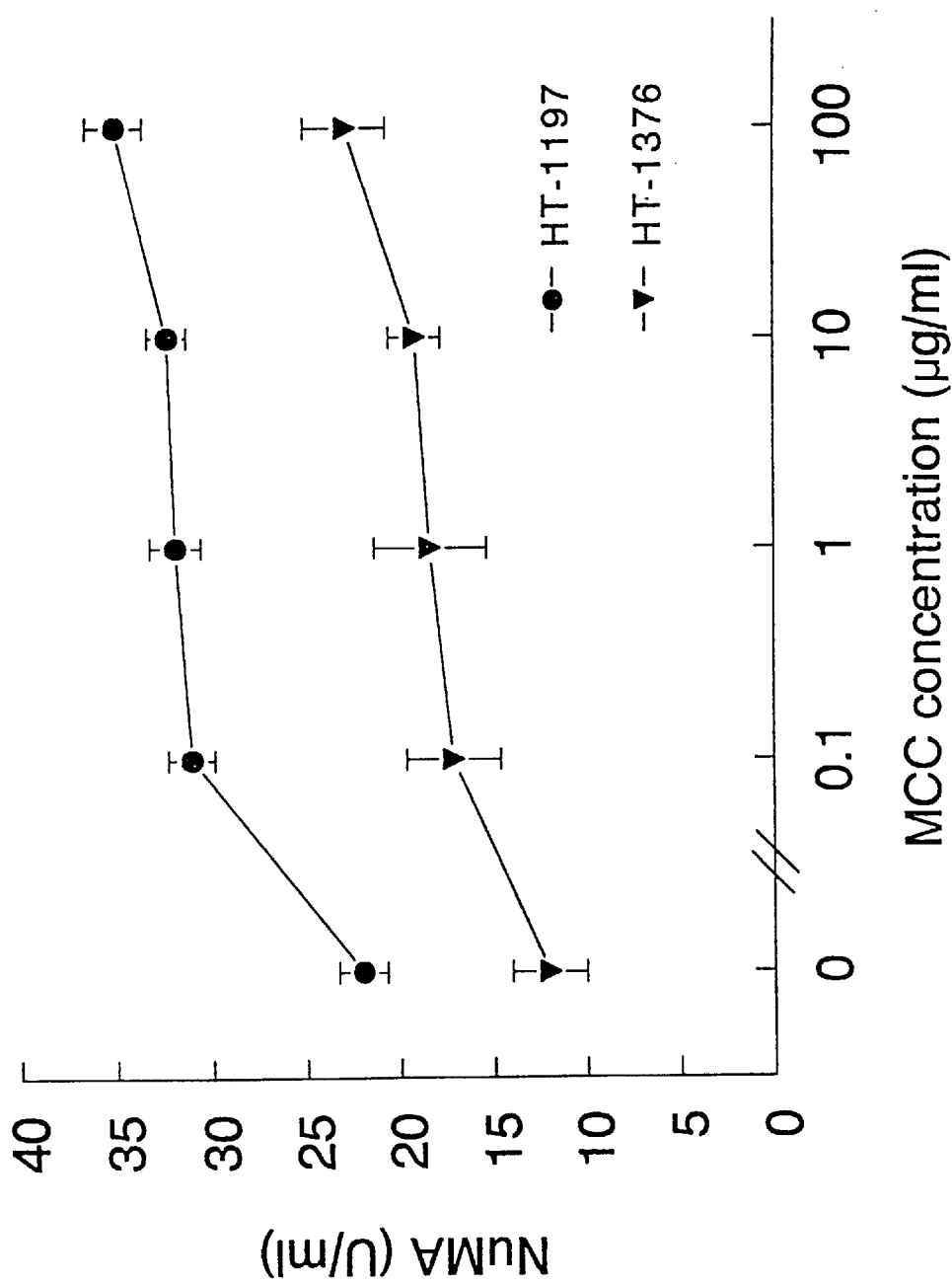
FIG. 5. Release of NuMA from HT-1197 and HT-1376 human bladder cancer cells with increasing concentrations of MCC. Results are the mean±SD of 3 independent experiments.
Figure 6A:
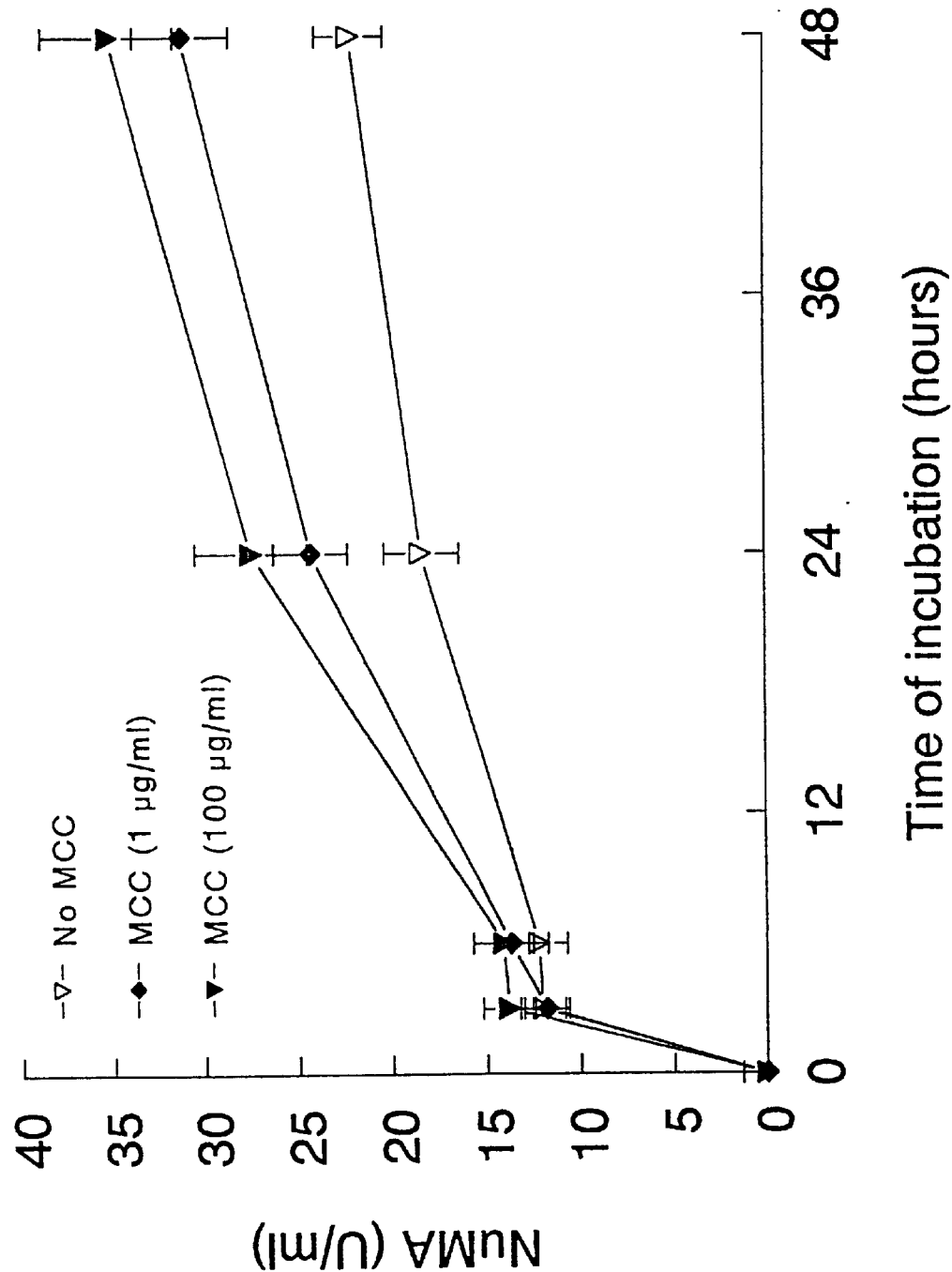
FIGS. 6A and 6B. Release of NuMA from HT-1197 (6A) and HT-1376 (6B) human bladder cancer cells with 1 $\mu$g/ml MCC or with 100 $\mu$g/ml MCC over 48 h. Results are the mean ±SD of 3 independent experiments.
Figure 6B:
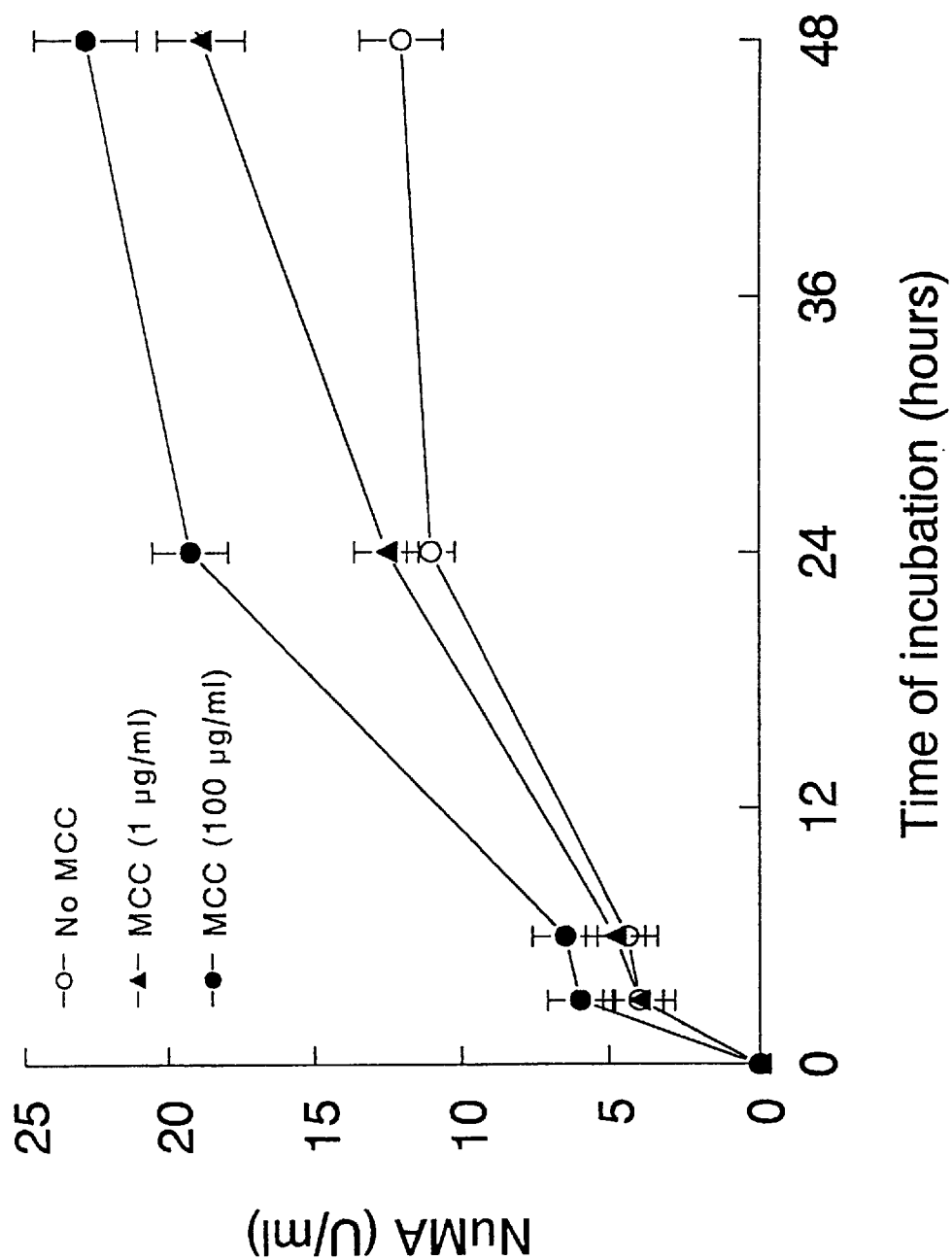

HT-1197 and HT-1376 human bladder cancer cells were incubated for 48 h with 0 μg/ml to 100 μg/ml of MCC. MCC induced the release of NuMA in a dose-related manner (FIG. 5). HT-1197 and HT-1376 human bladder cancer cells were incubated with 1 μg/ml or with 100 μg/ml of MCC for 48 h. Enhanced release of NuMA was detected within 24 hours after incubation of HT-1197 cells (FIG. 6A) and of HT-1376 (FIG. 6B) cells with 100 μg/ml of MCC.

Figure 7:
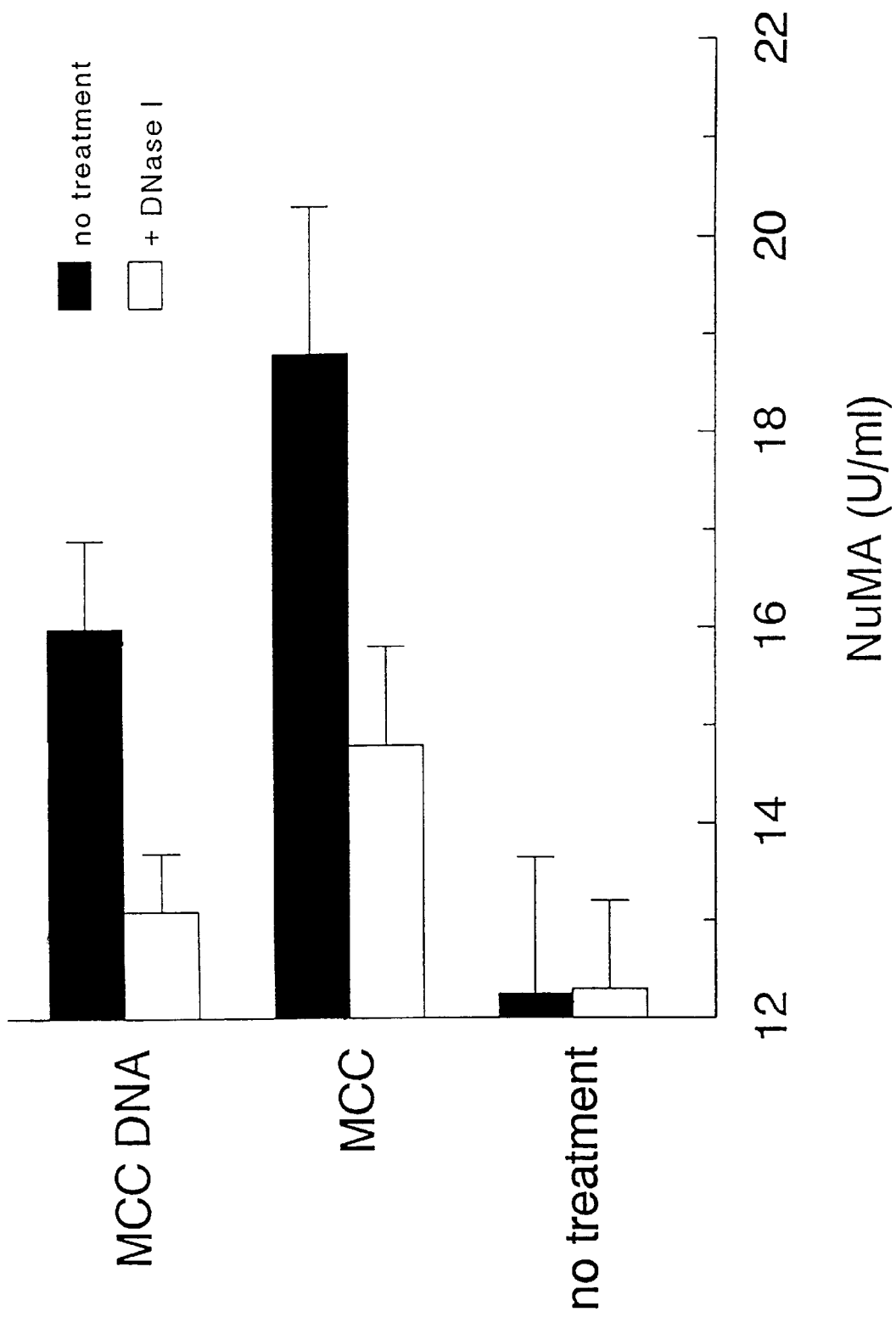
FIG. 7 Release of NuMA from HT-1376 human bladder cancer cells with 1 $\mu$g/ml untreated and DNase I treated MCC-DNA and MCC. Results are the mean±SD of 3 independent experiments.
Figure 8:
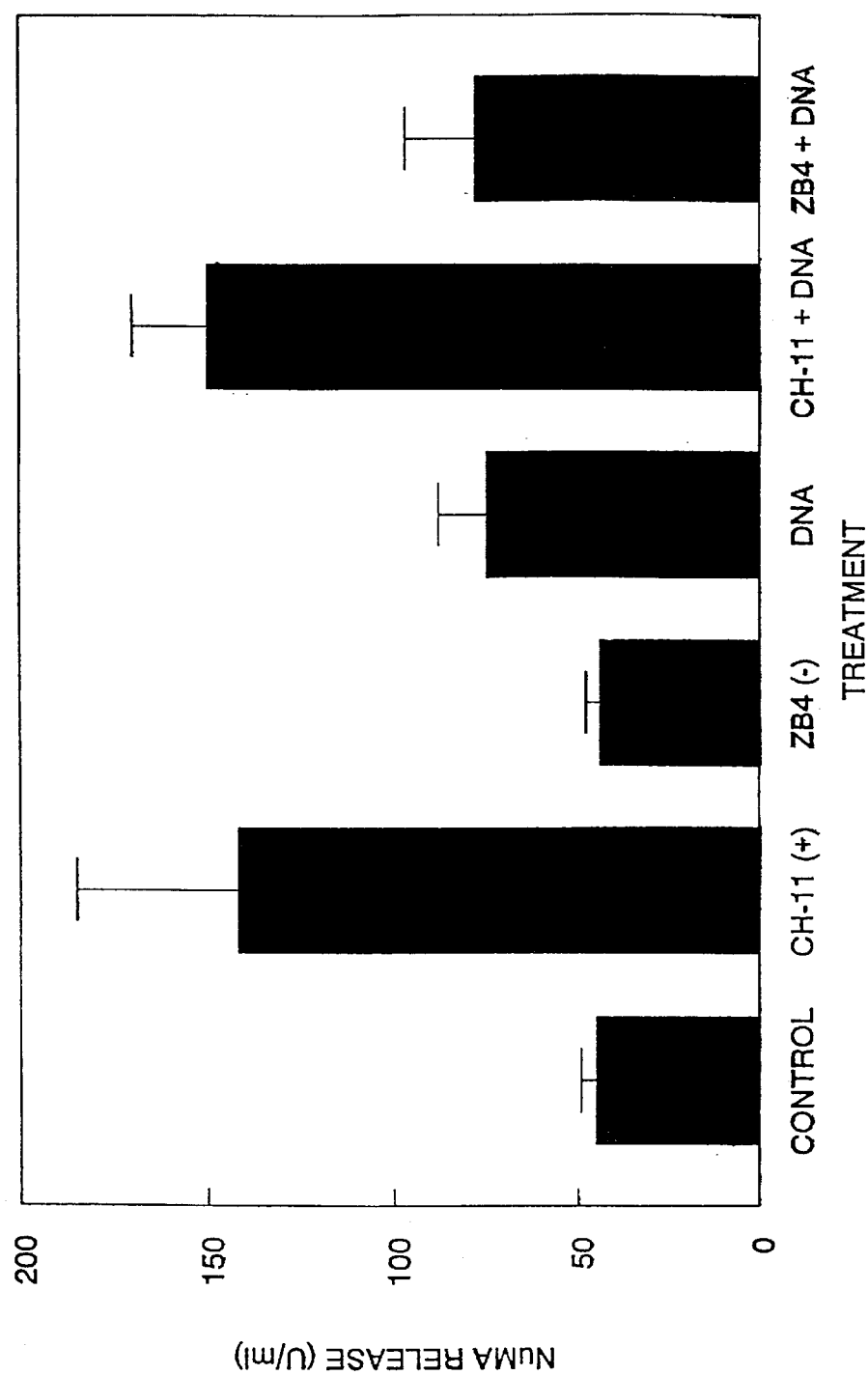
FIG. 8 NuMA release from Jurkat cells incubated with PBS, CH-11 antibodies, ZB4 antibodies, *M. phlei*-DNA, CH-11 antibodies+*M. phlei*-DNA and ZB4 antibodies+*M. phlei*-DNA.

HT-1197 human bladder cancer cells were incubated for 48 h with untreated and DNase I treated MCC-DNA and M-DNA. As shown in FIG. 7, MCC release of NuMA was significantly greater than MCC-DNA release of NuMA release. DNase I treatment significantly reduced NuMA release.

As determined by NuMA release, MCC induces apoptosis in HT-1197 and in HT-1376 human bladder cancer cells in a dose-dependent and in a time-dependent manner. That DNase I treatment reduces MCC and MCC-DNA induced apoptosis induction, suggests that the oligonucleotide structure of M-DNA is important for MCC and MCC-DNA induction of apoptosis in bladder cancer cells. MCC, wherein M-DNA is preserved and complexed on *M. phlei* cell wall, induces more apoptosis than MCC-DNA. This suggests that the presentation of M-DNA on *M. phlei* cell wall also is necessary for optimal induction of apoptosis in bladder cancer cells.

EXAMPLE 9
Fas Independent Induction of Apoptosis in Jurkat Human T Lymphoblast Cells by *M. phlei*-DNA.

Jurkat human T lymphoblast cells were incubated for 1 h with PBS, with 1 µg/ml CH-11 antibody, an antibody that binds to Fas and induces apoptosis (+control) (Coulter-Immunotech), and with 1 µg/ml ZB4 antibody, an antibody that binds to Fas and inhibits apoptosis (–control) (Coulter-Immunotech). *M. phlei*-DNA, 1 µg/ml, was added and NuMA release was determined after 48 h.

As shown in FIG. 7, *M. phlei*-DNA induced apoptosis both in the absence of and in the presence of ZB4 antibody. These data demonstrate that induction of apoptosis by M-DNA is independent of Fas.

EXAMPLE 10
Effect of MCC on Cell Proliferation and on Apoptosis in Various Cancer Cell Lines.

Table 2 summarizes the effects of MCC on inhibition of proliferation and on induction of apoptosis in cancer cells as determined by DNA fragmentation, NuMA release and flow cytometric analysis in human and murine cancer cell lines.

TABLE 2

Inhibition of proliferation and induction of apoptosis in human and murine cancer cell lines

| Cells | Inhibition of proliferation | Nucleosome-sized DNA | NuMA released | Flow cytometric analysis |
|---|---|---|---|---|
| THP-1 | yes | yes | yes | ND* |
| HL-60 | yes | yes | yes | ND |
| HL-60 MX-1 | yes | yes | yes | ND |
| RAW 264.7 | yes | yes | yes | ND |
| JURKAT | yes | yes | yes | ND |
| HT-1376 | yes | yes | yes | ND |
| HT-1197 | yes | yes | yes | ND |
| B-16-FI | yes | yes | ND | ND |
| SW260 | ND | ND | ND | yes |
| OC2 | ND | ND | ND | yes |
| LS1034 | yes | yes | yes | ND |

*ND = Not Done

MCC, wherein M-DNA is preserved and complexed on *M. phlei* cell wall, inhibits proliferation of and induce apoptosis in each of the cancer cell lines tested. These cancer cell lines include p53/p21 abnormal and drug resistant HT-1376 human bladder, atypical drug resistant HL-60 MX-1 human promyelocytic leukemia, Fas abnormal SW260 human colon, and conventional drug resistant LS1034 human cecum carcinoma cells.

EXAMPLE 11
MCC Activation of Caspase-3 in Human Leukemic THP-1 Monocytes

Caspase 3 is a key enzyme in the apoptotic pathway downstream of Fas-FasL signaling. To determine if MCC can by-pass Fas and directly activate the caspase cascade in cancer cells, the effect of MCC on caspase-3 activity was assayed in human leukemic THP-1 monocytes.

THP-1 monocytes ($2 \times 10^7$ cells) were incubated for 48 h with MCC (100 µg/ml). The THP-1 cells were lysed in 50 mM HEPES, pH 7.4, 100 mM NaCl, 0.1% (3-[3-cholamidopropyl)-dimethyl-ammonio]-1-propane-sulfonate, CHAPS, 10 mM DTT, 1 mM EDTA and 10% glycerol. Caspase-3 activity was determined with a commercial ELISA (BIOMOL Research Laboratories, Inc., Plymouth Meeting, Pa.), using the included substrate, inhibitor and purified caspase-3 enzyme. Results are expressed as optical densities read at 405 nm.

TABLE 3

MCC (100 µg/ml) activation of caspase 3 activity in human leukemic THP-1 monocytes

| | p-nitroanalide absorbance, 405 nm | |
|---|---|---|
| Incubation | O.D. × $10^{-1}$, 3 hours incubation | O.D. × $10^{-1}$, 6 hours incubation |
| THP-1 alone | 0.19 | 0.06 |
| THP-1 + MCC cell extract | 0.44 | 0.20 |
| THP-1 + MCC treated with DNase cell extract | 0.12 | 0.11 |
| Purified Caspase-3 | 0.87 | 0.58 |
| Purified Caspase-3 + caspase-3 inhibitor | 0.00 | 0.00 |
| THP-1 + MCC cell extract + Caspase-3 inhibitor | 0.00 | 0.00 |

As shown in Table 3, incubation with MCC resulted in a 232% (3 h) and 333% (6 h) increase in caspase-3 and caspase-3 like activity in human leukemic THP-1 monocytes. MCC induction of caspase-3 and caspase-3 like activity was abolished by DNase I treatment of MCC. Specificity of MCC was demonstrated using caspase-3 inhibitor. Addition of caspase-3 inhibitor to MCC-treated THP-1 cell extract completely abolished measurable caspase-3 and caspase-3 like activity. MCC induction of caspase-3 and caspase-3 like activity is novel and unexpected. To stimulate caspase-3 and caspase-3 like activity, MCC must first enter the responsive cells and them initiate the lethal proteolytic cascade of apoptosis execution.

EXAMPLE 12
Effect of TAMOXIFEN on MCC Inducted Apoptosis in Human Leukemic THP-1 Monocytes Human leukemic THP-1 monocytes were incubated for 90 min in control medium or in medium containing 10 µg/ml ((Z)-2-[p-(1,2-Diphenyl-1-butenyl)-phenoxy]-N,N-dimethylethylamine), TAMOXIFEN (Sigma-Aldrich), an anti-estrogen used in the palliative treatment of advanced breast cancer. Cells were washed extensively with ice-cold medium (2×), resuspended to about $10^6$ cells/ml in medium and incubated for 48 h with 0, 1, 10 and 100 µg/ml of MCC. Apoptosis was quantitated by measuring NuMA.

TABLE 4

Effect of tamoxifen on MCC induced apoptosis in human leukemic THP-1 monocytes determined by NuMA release in U/ml.

| | + MCC 1 µg/ml | + MCC 10 µg/ml | + MCC 100 µg/ml | + medium only |
|---|---|---|---|---|
| Control | 174.6 | 260.0 | 237.2 | 174.6 |
| TAMOXIFEN (10 µg/ml) | 354.9 (↑50.8%) | 406.2 (↑36.0%) | 410.0 (↑42.1%) | 284.7 |

As shown in Table 4, preincubation in TAMOXIFEN significantly increased MCC induced apoptosis at each of the MCC concentrations used. These data demonstrate that MCC can be used as an adjunct to other anti-cancer agents to increase treatment effectiveness.

EXAMPLE 13
Modification of M-phlei-DNA by Methylation, Sonication and Autoclaving Cytosine methylation of BCG with CpG methylase abolishes BCG anti-cancer activity (Krieg et al. Nature 374:546–549, 1995). Therefore, the effect of CpG methylation on the ability of M. phlei-DNA to induce apoptosis was determined.

M. phlei-DNA, 1 µg, was methylated using 2.5 U of CpG Sss I methylase (New England Biolabs, Mississauga, Ontario, Canada) and the completeness of the methylation was confirmed by electrophoresis in 0.5% agarose gel for 3 h at 100 V.

Figure 9:
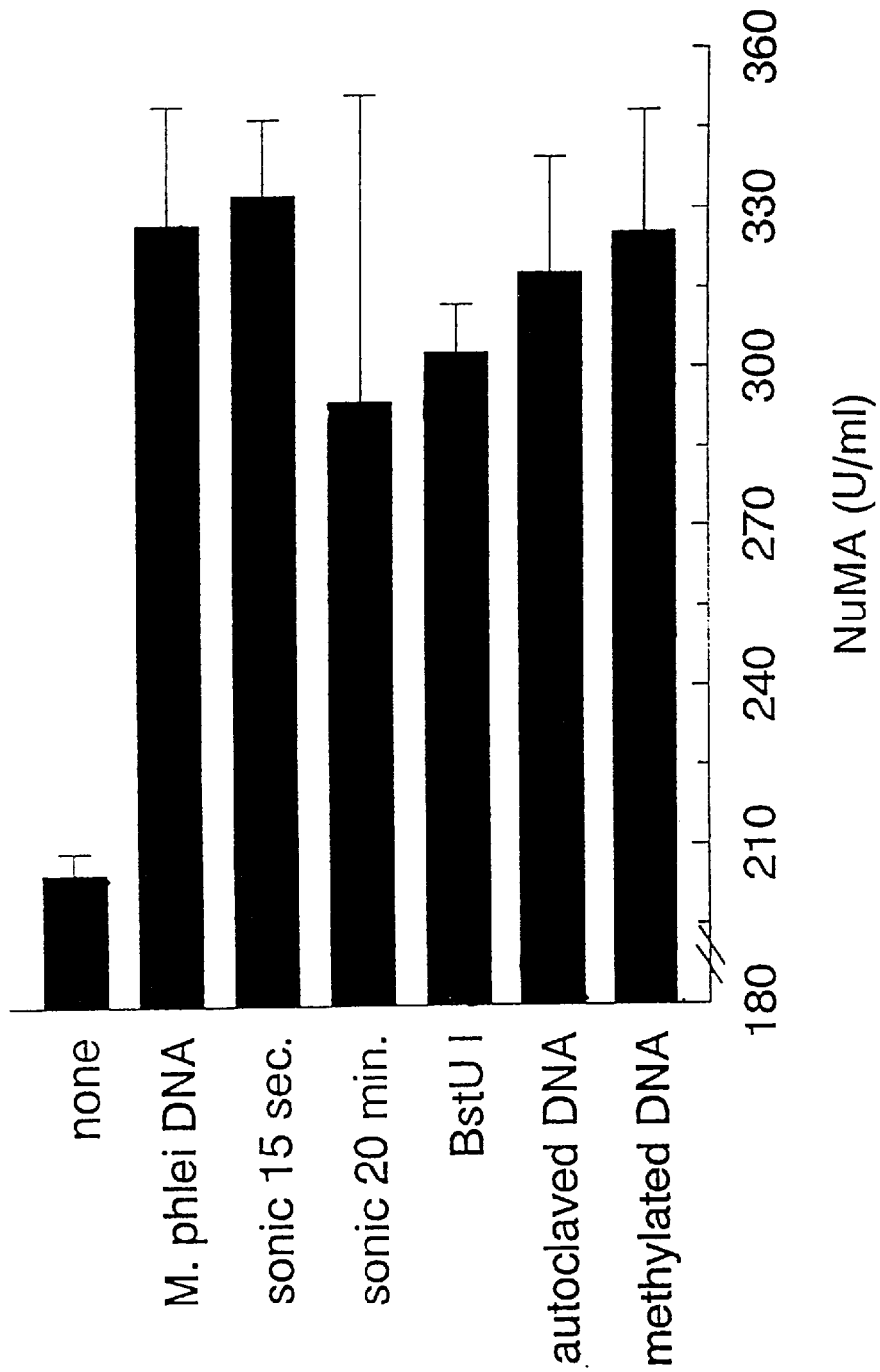
FIG. 9. NuMA release from human leukemic THP-1 monocytes by *M. phlei*-DNA and by sonicated, BstU I cleaved, autoclaved and methylated *M. phlei*-DNA.

As shown in FIG. 9, methylation did not effect M. phlei-DNA induced NuMA release from human leukemic THP-1 monocytes. Therefore, unlike BCG, CG-motifs are not necessary for apoptosis induction by M. phlei-DNA.

The oligonucleotide length of M phlei-DNA (1 µg) was reduced by sonication for 15 sec or for 20 min on ice in a Model W-38 ultrasonic processor (HeatSystems-Ultrasonics, Inc.), by autoclaving at 121° C. for 30 min (Castle Sybron MDT, Dubuque, Iowa) or by digestion with BstU I restriction endonuclease. Sonication, autoclaving and BstU I digestion, each of which reduces oligonucleotide length to the range of about 5 base pairs to about 250 base pairs, did not change M. phlei-DNA induced release of NuMA from THP-1 monocytes (FIG. 9). Similar results were obtained with MCC. These results demonstrate that M. phlei-DNA and MCC induce apoptosis in cancer cells, even at short oligonucleotide length (about 5 base pairs to about 250 base pairs).

Human leukemic THP-1 monocytes were incubated for 48 h with untreated MCC and M. phlei-DNA and with MCC and M. phlei-DNA autoclaved for 30 min at 121° C. Autoclaving did not affect the ability of MCC or of M. phlei-DNA to inhibit of proliferation of (Table 5A), or to induce apoptosis in (Table 5B) human leukemic THP-1 monocytes.

TABLE 5A

Effect of autoclaving on MCC and M. phlei-DNA inhibition of proliferation

|  | Non-autoclaved % inhibition | Autoclaved % inhibition |
|---|---|---|
| MCC 1 µg/ml | 87 ± 4 | 84 ± 10 |
| MCC 10 µg/ml | 68 ± 1 | 74 ± 6 |
| MCC 100 µg/ml | 59 ± 7 | 64 ± 6 |
| M. phlei -DNA* 1 µg/ml | 88 ± 8 | 84 ± 11 |
| M. phlei -DNA 10 µg/ml | 80 ± 8 | 74 ± 6 |
| M. phlei -DNA 100 µg/ml | 68 ± 4 | 64 ± 5 |

TABLE 5B

Effect of autoclaving on MCC and M. phlei-DNA induction of apoptosis determined by NuMA release in U/ml.

|  | Non-autoclaved | Autoclaved |
|---|---|---|
| MCC 1 µg/ml | 298.0 | 277.1 |
| MCC 10 µg/ml | 325.9 | 322.4 |
| MCC 100 µg/ml | 339.9 | 357.3 |
| M. phlei -DNA * 100 µg/ml | 261.4 | 268.4 |
| M. phlei -DNA 10 µg/ml | 317.2 | 278.4 |
| M. phlei -DNA 1 µg/ml | 306.8 | 285.8 |

EXAMPLE 14
MCC Inhibits Cancer Growth in vivo

MCC and DNase I treated MCC were emulsified to a final concentration of 1 mg/ml in PBS containing 2% w/v mineral oil and 0.02% w/v TWEEN 80 (Fisher Chemical Co.) by sonication at 4° C. for 5 min. (Heat Systems-Ultrasonics, Inc.).

Line 10 hepatoma cells, syngenic for strain-2-guinea pigs were rapidly thawed, washed by centrifugation and resuspended in M199 medium to a concentration of $10^6$ cells/ml. One-tenth ml containing $1.5 \times 10^6$ cells was injected intradermally into the flanks of 3 month-old strain 2 guinea pigs. Treatment was initiated 6 to 7 days post-injection, when the cancers were between about 0.5 and about 0.8 cm in diameter. Seven animals were treated with emulsification buffer alone (control), 7 with emulsification buffer containing MCC, and 7 with emulsification buffer containing DNase I treated MCC. The emulsions were instilled directly into the cancer and surrounding normal tissue. One-half ml of emulsion was administered at 0 h and at 6 h for a total volume of 1 ml containing 1 mg of MCC or of DNase I treated MCC.

Cancer diameters (longest diameter+shortest diameter) were recorded weekly for 3 weeks. Cancer volumes were calculated in $mm^3$ as 0.5×a (longest diameter)×$b^2$ (shortest diameter) and the increase in cancer volume relative to day 0 of treatment was calculated for each guinea pig. Statistical analysis was done using 2-way ANOVA with replicates (PHARM/PCS version 4.2, MCS, Philadelphia, Pa.). Differences in treatment were considered significant at $p \leq 0.05$.

Figure 10:
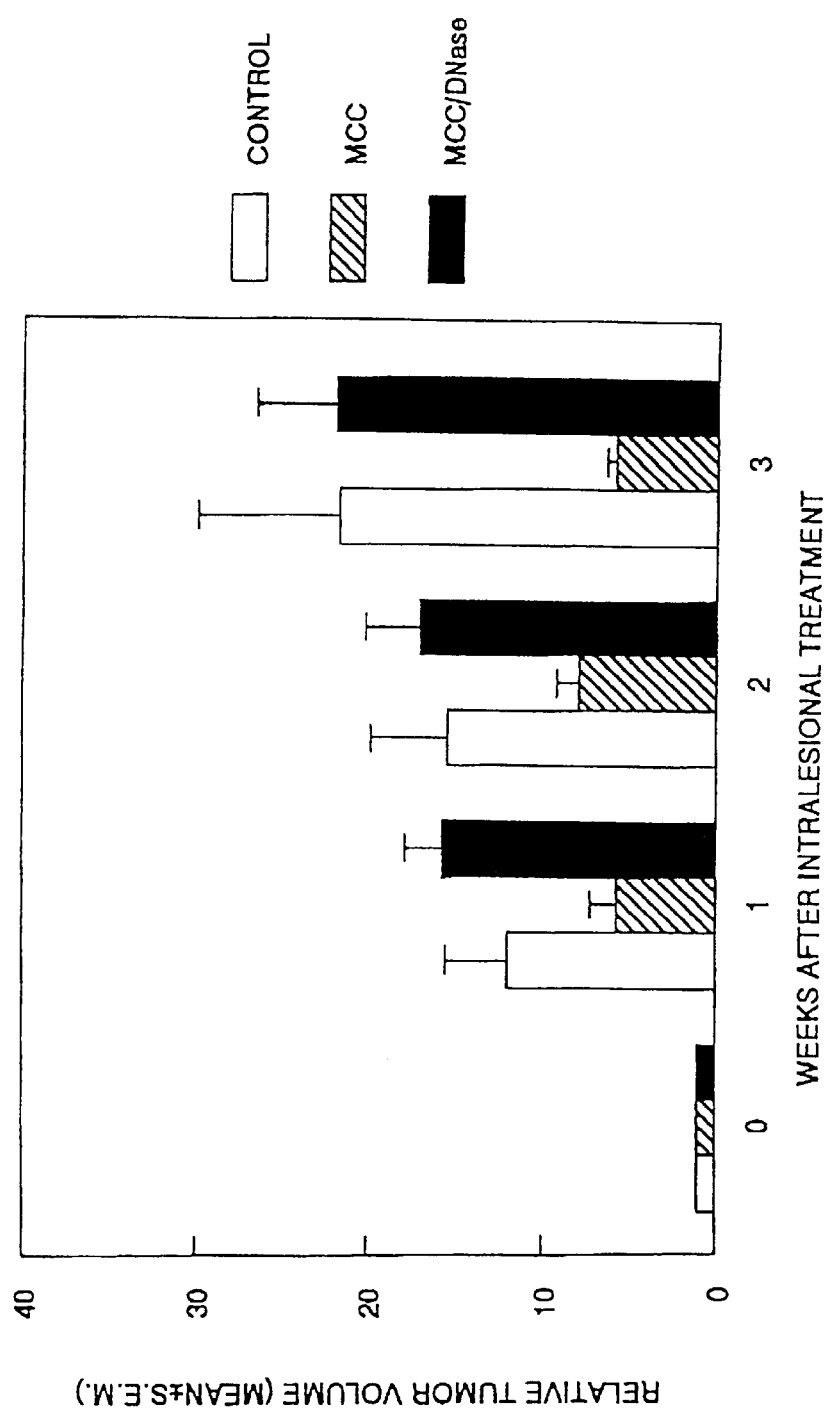
FIG. 10. In vivo anti-cancer activity of MCC and of DNase I treated MCC in line 10 hepatoma in guinea pigs. Results are the mean±SD of 7 animals in each experimental group.
Figure 11:
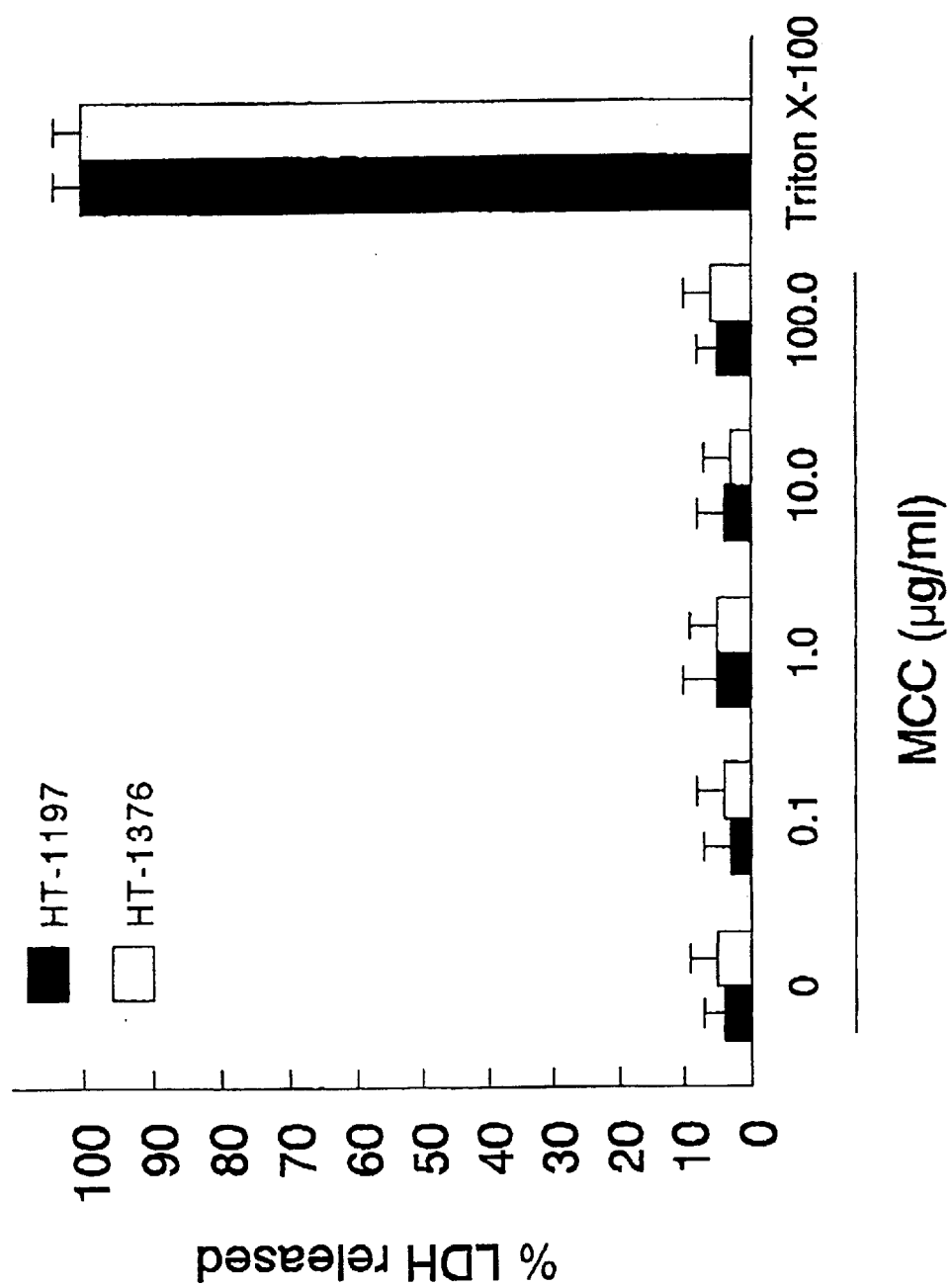
FIG. 11. Percentage LDH release by HT-1197 and HT-1376 human bladder cancer cells as an indicator of MCC cytotoxicity. Results are the mean±SD of 3 independent experiments.

As shown in FIG. 21, with control emulsion, cancer volume increased by about 22-fold by week 3, whereas with MCC, cancer growth was significantly inhibited compared to control emulsion (FIG. 10, Table 6). With DNase I treated MCC, cancer growth was not significantly different from control (FIG. 10, Table 6).

TABLE 6

Two-way ANOVA with replicates

| Treatment comparison | p value |
|---|---|
| Control vs MCC | p < 0.01 |
| Control vs MCC + DNase | Not significant |
| MCC vs MCC + DNase | p < 0.01 |

These data show that instillation of MCC at the site of a tumor results in regression of the tumor. Moreover, the significant (p<0.01) difference in inhibition of cancer growth between MCC and DNase I treated MCC shows that the M-DNA, which is preserved and complexed on the surface of the M. phlei cell wall, is necessary for the anti-cancer activity of MCC in vivo.

EXAMPLE 15
MCC Cytotoxicity

Cell cytotoxicity is characterized by the loss of plasma membrane integrity and release of cytoplasmic enzymes such as, but not limited to, LDH (Wyllie et al. International Review of Cytology 68: 251–306, 1980; Phillips et al. Vaccine 14:898–904, 1996). Human bladder cancer cells release LDH when treated with cytotoxic agents (Rahman M. Urology International 53:12–17, 1994).

To assess the cytotoxicity of MCC, HT-1197 and HT-1376 human bladder cancer cells were incubated for 48 h with from 0 µg/ml to 100 µg/ml of MCC or with lysing buffer (10 mM Tris, 1 mM EDTA, 0.2% +octylphenoxypolyethoxyethanol TRITON X-100, pH 7.5)

as a control for total LDH release (Filion et al. Biochim Biophys Acta 1329:345–356, 1997). LDH release into the culture supernatant was determined using a commercial assay (Sigma-Aldrich).

As determined by LDH release, MCC was not cytotoxic to HT-1197 or to HT-1376 cells (FIG. 22). The absence of cytotoxicity demonstrates that MCC acts directly on human bladder cancer cells to inhibit proliferation and to induce apoptosis.

EXAMPLE 16
Effect of MCC on IL-6 and IL-12 Production by Human Monocytes and Murine Macrophages MCC Stimulation of cytokine production IL-12 did not inhibit proliferation of or induce apoptosis in human bladder cancer cells (Examples 6 & 7). However, some bladder cancer cells are reported to secrete cytokines (DeReijke et al. Urology Research 21:349–352, 1993; Bevers et al. British Journal of Urology 80:35–39, 1997). Moreover, the cytokine IL-12 is reported to have anti-cancer activity against some bladder cancer cells (Voest et al. Journal National Cancer Institute 87:581–586, 1995; Stine et al. Annals NY Academy of Science 795:420–421, 1996), whereas the cytokine GM-CSF is reported to have pro-cancer activity toward some bladder cancer cells (Hawkyard et al. Journal of Urology 150:514–518, 1993).

Therefore, the effect of MCC on IL-6, IL-12 and GM-CSF synthesis by HT-1197 and HT 1376 human bladder cancer cells and by human THP-1 monocytes, murine macrophages, murine RAW 264.7 monocytes, and murine spleen cells was determined. Cytokine production was determined in pg/ml in 100 μl of culture supernatant using the appropriate commercial ELISA (BioSource, Camarillo Calif.). The IL-12 ELISA measures both IL-12 p70 complex and free p40 subunit.

Figure 12:
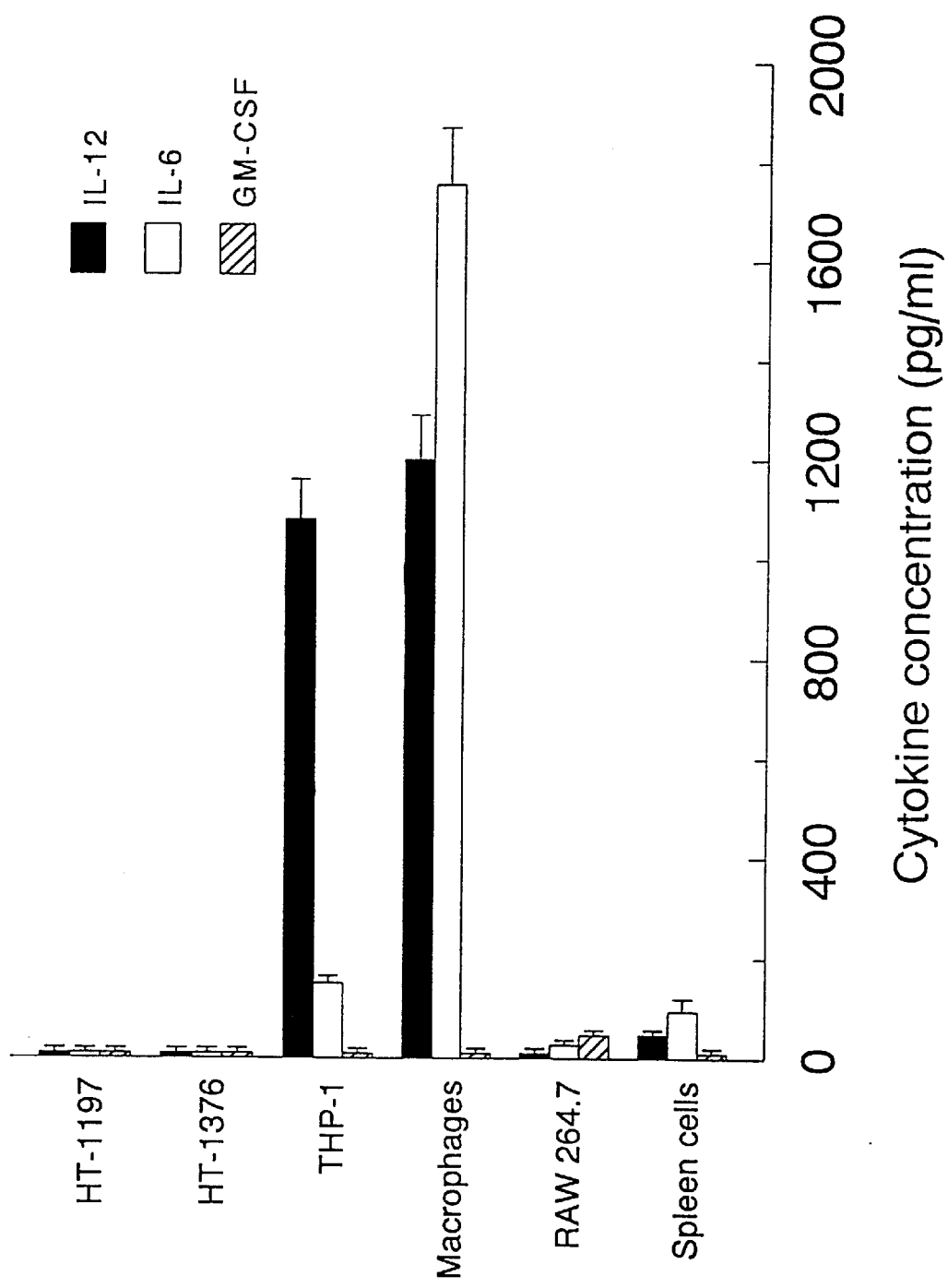
FIG. 12. Stimulation of IL-6, IL-12 and GM-CSF production in human HT-1197 and HT-1376 bladder cancer cells, human THP-1 monocytes, murine macrophages, murine RAW 264.7 monocytes and murine spleen cells by MCC. Results are the mean±SD of 3 independent experiments.

HT-1197, HT-1376, THP-1, macrophage, RAW 264.7, and murine spleen cells were incubated for 48 h with 1 μg/ml MCC. As shown in FIG. 12, MCC stimulated production of IL-6 and of IL-12 by human monocytes and murine macrophages, but not by human bladder cancer cells, murine monocytes or spleen cells. MCC did not stimulate GM-CSF production of in any of the cancer cells tested.

These data show that MCC stimulates production of the anti-cancer cytokines IL-6 and IL-12 by human monocytes and murine macrophages. MCC does not stimulate cytokine production by human bladder cancer cells. MCC does not stimulate production of the pro-cancer cytokine GM-CSF.

EXAMPLE 17
Effect of Untreated and DNase I Treated MCC, M. phlei-DNA, MCC-DNA and REGRESSIN® on IL-12 Production by Human THP-1 Monocytes Human THP-1 monocytes were incubated for 48 h with MCC, M-phlei-DNA, MCC-DNA and REGRESSIN® before treatment with DNase I, after treatment with DNase I, and after addition of M-DNA to DNase I treated MCC, M. phlei-DNA and MCC-DNA.

TABLE 7

IL-12 production in pg/ml by human THP-1 monocytes

| | IL-12 production, pg/ml culture supernatant | | | |
|---|---|---|---|---|
| | M. phlei-DNA | MCC-DNA | MCC | Regressin ® |
| Treatment None | 1 μg/ml 407 | 1 μg/ml 676 | 1 μg/ml 1222 | 1 μg/ml 196 |

TABLE 7-continued

IL-12 production in pg/ml by human THP-1 monocytes

| | IL-12 production, pg/ml culture supernatant | | | |
|---|---|---|---|---|
| | M. phlei-DNA | MCC-DNA | MCC | Regressin ® |
| Treatment DNase | 1 μg/ml 178 | 1 μg/ml 367 | 1 μg/ml 729 | 1 μg/ml 200 |
| DNase + 1 μg DNA | 424 | 658 | 783 | Not Done |

As shown in Table 7, MCC, M. phlei-DNA and MCC-DNA each stimulated THP-1 monocytes to produce IL-12. MCC stimulated more IL-12 production than M. phlei-DNA and MCC-DNA. Regressin stimulated significantly less IL-12 production. DNase I treatment reduced by about 50% MCC, M. phlei-DNA and MCC-DNA stimulated IL-12 production. Regressin® was not effected by DNase I treatment. Addition of MCC-DNA to DNase I-treated MCC did not restore its stimulation of IL-12 production, whereas addition of M. phlei-DNA to DNase I-treated M. phlei and of MCC-DNA to DNase I treated MCC-DNA did restore their stimulation of IL-12 production.

These data show that M-DNA, as MCC, M. phlei-DNA or MCC-DNA, stimulates production of the cytokine IL-12 by human monocytes. MCC stimulates more IL-12 production than M. phlei-DNA or MCC-DNA, suggesting that the carrier on which M-DNA is presented to the monocytes can optimize their response. DNase I treatment, which degrades the M-DNA, reduces significantly M. phlei-DNA, MCC-DNA and MCC stimulated IL-12 production, suggesting that the oligonucleotide structure of M-DNA is important for its activity. Addition of M-DNA to DNase I treated MCC did not restore its stimulation of IL-12 production, suggesting that the physical association of M-DNA with M. phlei cell wall also is important for optimal stimulation of IL-12 production by human monocytes.

Human THP-1 monocytes were incubated for 48 h with 0.5, 1.0. 1.5 and 5.0 μg/ml of MCC and of REGRESSIN®.

TABLE 8

IL-12 production in pg/ml by human THP-1 monocytes

| | MCC | REGRESSIN ® |
|---|---|---|
| 0.5 μg/ml | 614 ± 30 | 65 ± 11 |
| 1.0 μg/ml | 1078 ± 40 | 223 ± 20 |
| 2.5 μg/ml | 1237 ± 82 | 313 ± 23 |
| 5.0 μg/ml | 1231 ± 112 | 359 ± 43 |

EXAMPLE 18
Effect of CD14 Antibody Treatment on MCC and MCC-DNA Stimulated IL-12 Production by Human THP-1 Monocytes Human THP-1 monocytes were incubated with PBS or with 10 μg/ml of anti-CD14 antibody (clone MY4, Coulter-Immunotech, Hialeah, Fla.) for 1 h. Then, 5 μg/ml of MCC or of MCC-DNA were added and the incubation was continued for 48 h. CD14 antibodies, which bind to CD14 receptors on the cell surface, caused about a 20% decrease in MCC and about an 85% decrease in MCC-DNA stimulated IL-12 production. (FIG. 2).

EXAMPLE 19
Effect of Cytochalasin D on MCC, M. phlei-DNA and MCC-DNA Stimulated IL-12 Production by Human THP-1 Monocytes Human THP-1 monocytes were incubated for 48 h with PBS or with 1 µg/ml MCC, *M. phlei*-DNA or MCC-DNA in the absence of and in the presence of 10 µg/ml of cytochalasin D (Sigma Chemical Co.). Cytochalasin D, which inhibits phagocytosis, caused about a 55% decrease in MCC, about a 65% decrease in *M-phlei*-DNA, and about a 50% decrease in MCC-DNA stimulated IL-12 production (FIG. 14).

Figure 13:
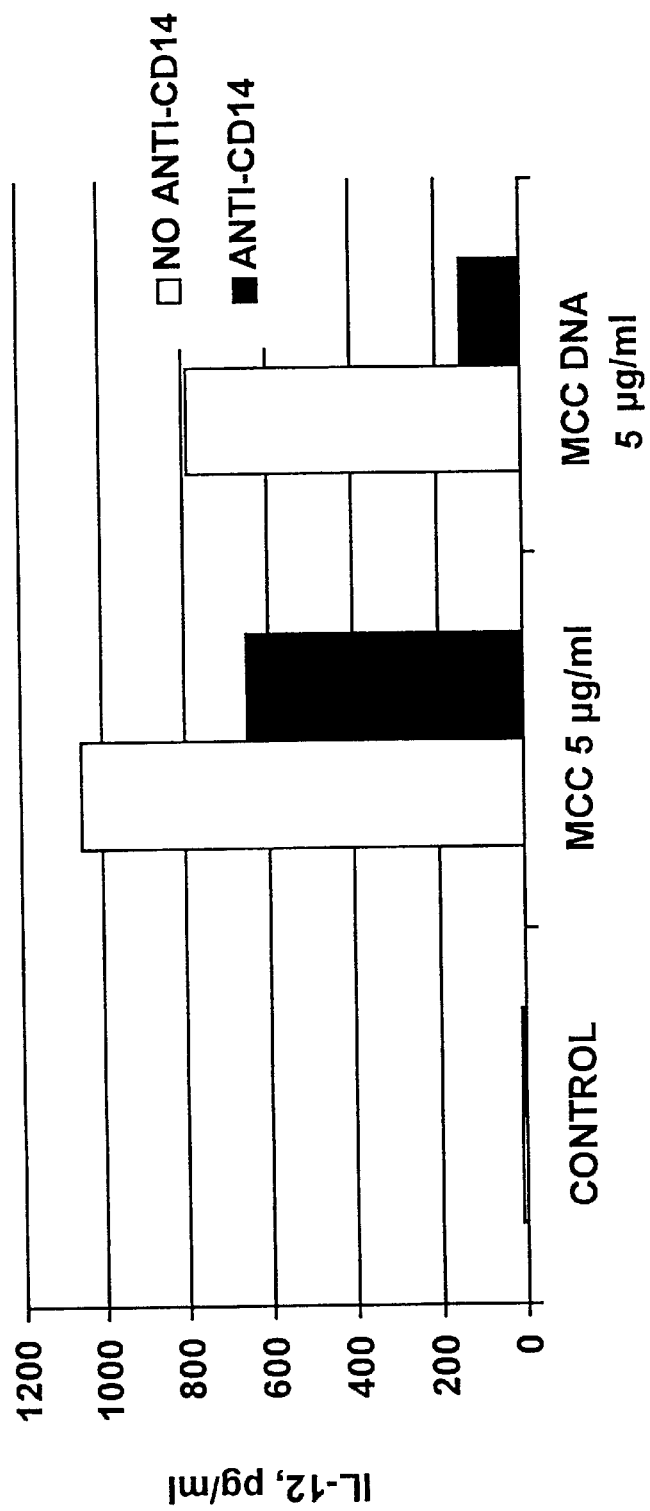
FIG. 13. Stimulation of IL-12 production in human THP-1 monocytes by MCC and MCC-DNA in the absence and in the presence of CD14 antibodies.
Figure 14:
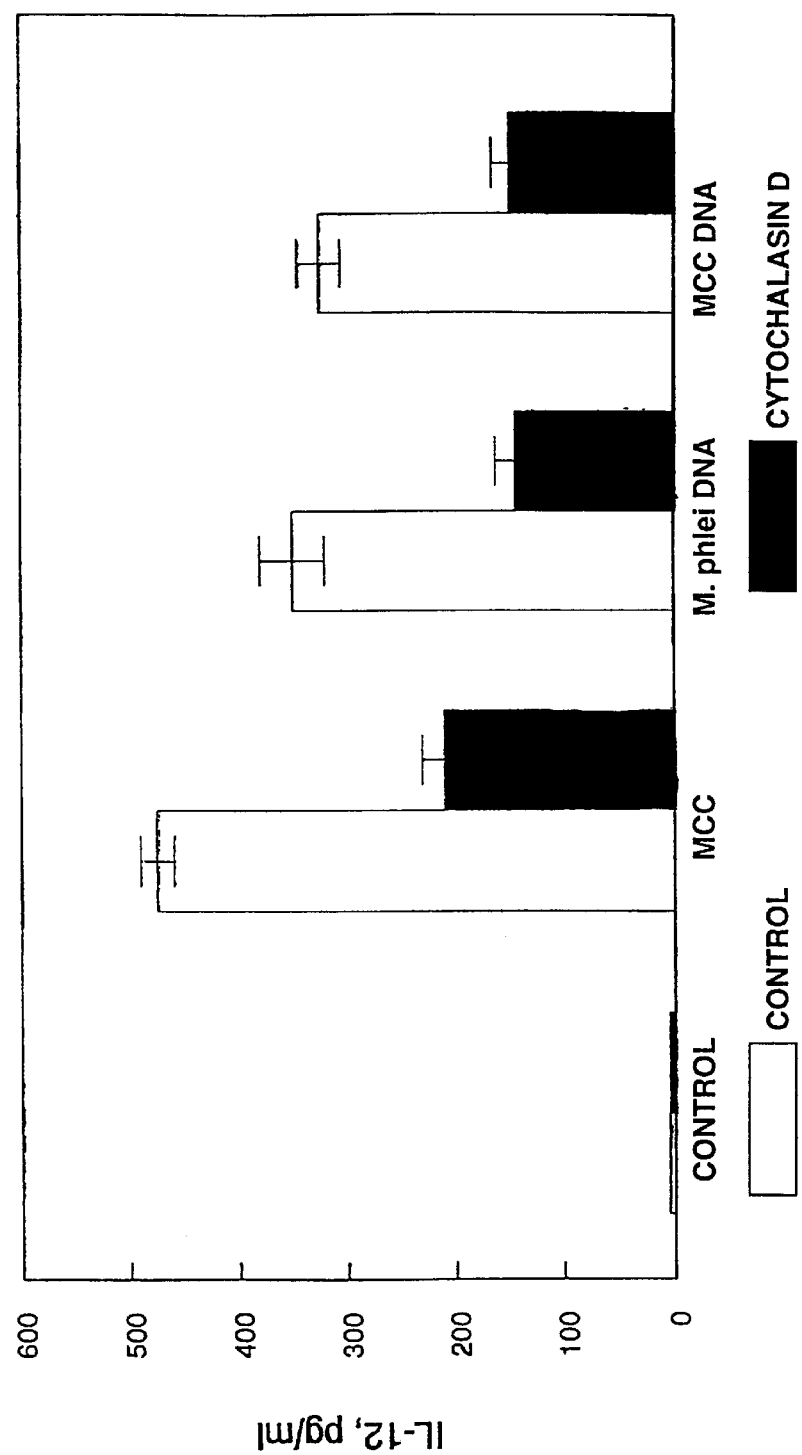
FIG. 14. Stimulation of IL-12 production in human THP-1 monocytes by MCC, *M. phlei*-DNA and MCC-DNA in the absence and in the presence of cytochalasin D.

Although not willing to be bound by the following hypothesis, but based on the data shown in FIGS. 13 & 14, it is believed that MCC, MCC-DNA and *M. phlei*-DNA interact with monocytes by more than one mechanism. FIG. 13 suggests they interact with the GPI-linked membrane receptor CD14 and are internalized. This mechanism is more specific for soluble MCC-DNA and *M. phlei*-DNA than for insoluble MCC. FIG. 14 suggests they interact with phagocytic receptors, such as the scavenger receptor, and are internalized. This mechanism is more specific for insoluble MCC than for soluble MCC-DNA and *M. phlei*-DNA.

EXAMPLE 20

Effect of CG Sequence and of MCC on IL-12 Production by Human THP-1 Monocytes

BCG nucleic acid is reported to stimulate lymphocyte proliferation, secretion of IL-6 and IL-12 by B-lymphocytes, secretion of IL-12 by monocytes, secretion of IL-6 and interferon-gamma by T-lymphocytes and secretion of interferon-gamma by NK cells (Klinman et al. Proceeding of the National Academy of Science USA 93:2879–2883, 1996). The active constituent in BCG nucleic acid has been identified as the palindromic oligonucleotide sequence purine-purine-C-G-pyrimidine-pyrimidine (CG motif).

Human THP-1 monocytes were incubated for 48 h with 0.5, 1 and 5 µg/ml of MCC or of 5'-GCTAGACGTTAGCGT-3' (SEQ ID NO:1) DNA prepared by solid phase synthesis using an automated DNA synthesizer.

TABLE 9

Effect of CG-containing oligonucleotide and of MCC on IL-12 production in pg/ml by THP-1 monocytes

|  | 5 µg/ml | 1 µg/ml | 0.5 µg/ml |
| --- | --- | --- | --- |
| GCTAGACGTTAGCGT (SEQ ID NO:1) | Undetectable | Undetectable | Undetectable |
| MCC | Not Done | 1239 | Not Done |

As shown in Table 9, the CG-containing oligonucleotide did not stimulate IL-12 production at any of the three concentrations tested, whereas MCC at 1 µg/ml had a significant stimulatory effect on IL-12 production by human monocytes.

EXAMPLE 21

Effect of Autoclaving on MCC and *M. phlei*-DNA Stimulation of IL-12 Production by Human THP-1 Monocytes Human THP-1 monocytes were incubated for 48 h with MCC and *M. phlei*-DNA and with MCC and *M. phlei*-DNA, which had been autoclaved for 30 min in sterile water.

TABLE 10

Effect of autoclaving on MCC and *M. phlei*-DNA stimulation of IL-12 production in pg/ml by THP-1 monocytes

|  | Non-autoclaved | Autoclaved |
| --- | --- | --- |
| MCC 1 µg/ml | 1017.4 | 905.2 |
| MCC 10 µg/ml | 1061.6 | 1076.8 |
| *M. phlei* -DNA 1 µg/ml | 902.0 | 1088.6 |
| *M.phlei* -DNA 10 µg/ml | 1027.1 | 949.5 |

As shown in Table 10, autoclaving, which reduces the size of M-DNA (MCC and *M. phlei*-DNA) oligonucleotides, does not effect the ability of MCC or of *M. phlei*-DNA to stimulate IL-12 production by human monocytes.

EXAMPLE 22

Effect of Heat Treatment and of DNase I Treatment on MCC, *M. phlei*-DNA, MCC-DNA and REGRESSIN® Stimulation of IL-12 Production by Murine Macrophages Murine peritoneal macrophages were incubated for 48 h with untreated MCC, *M. phlei*-DNA, MCC-DNA and REGRESSIN® and with *M. phlei*-DNA, MCC-DNA and REGRESSIN®, which had been heated at 100° C. for 10 minutes and then cooled in ice for 2 minutes.

TABLE 11

IL-12 production in pg/ml by murine macrophages.

|  | IL-12 production, pg/ml supernatant | | |
| --- | --- | --- | --- |
| Treatment | 12.5 µg/ml | 5.0 µg/ml | 0.1 µg/ml |
| *M. phlei*-DNA | 228 | 207 | 140 |
| *M phlei*-DNA heat-treated | 278 | 222 | 164 |
| MCC-DNA | Not Done | 176 | 164 |
| MCC-DNA heat-treated | Not Done | 235 | 131 |
| MCC | Not Done | 745 | Not Done |
| REGRESSIN ® | 110 | 96 | 80 |
| REGRESSIN ® heat-treated | 93 | 82 | 79 |

As shown in Table 11, at a concentration of 5 µg/ml, IL-12 production was stimulated most by MCC, less by *M. phlei*-DNA and MCC-DNA, and least by REGRESSIN®. Heat treatment of *M. phlei*-DNA, MCC-DNA and REGRESSIN® had no significant effect on their stimulation of IL-12 production. Although not shown, heat treatment of MCC caused a slight, but significant, increase in IL-12 production.

Figure 15:
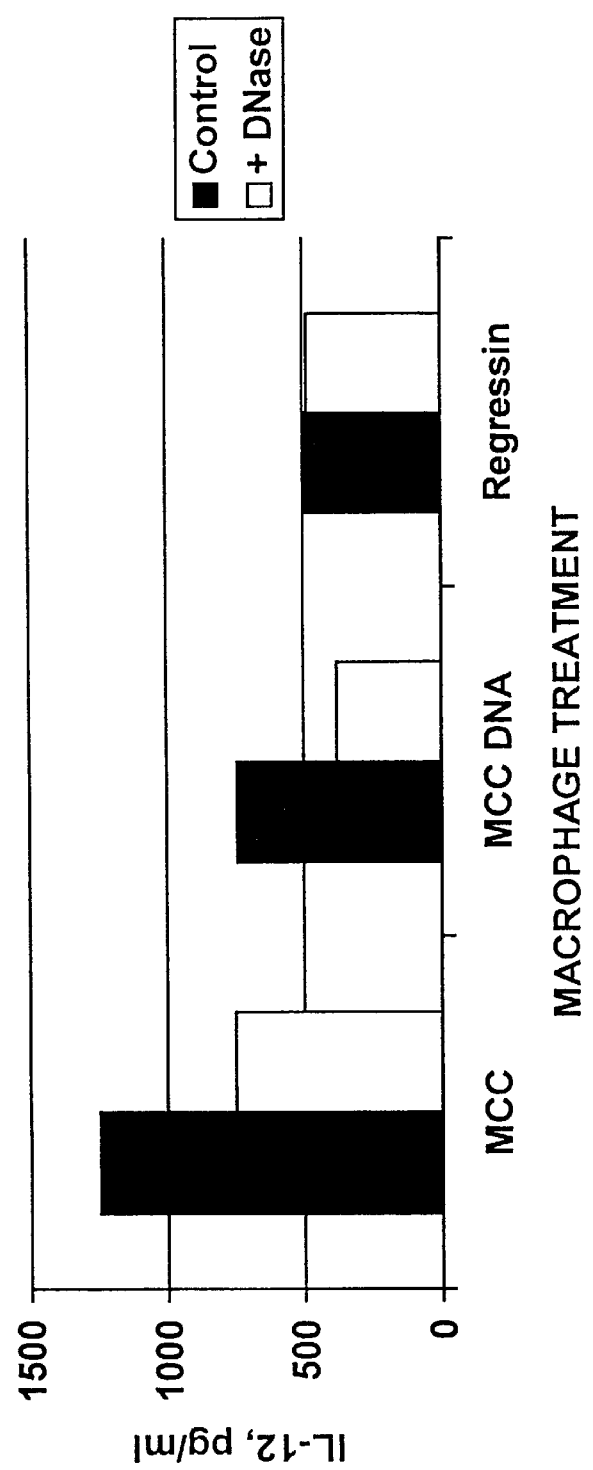
FIG. 15. Stimulation of IL-12 production in murine macrophages by MCC, MCC-DNA and REGRESSIN® before and after DNase I treatment.

Murine peritoneal macrophages were incubated for 48 h with untreated and with DNase I treated MCC, MCC-DNA and REGRESSIN® (FIG. 15). IL-12 production was stimulated most by MCC, less by MCC-DNA and least by REGRESSIN®. DNase I treatment of MCC and of MCC-DNA significantly reduced their stimulation of IL-12 production, whereas DNase I treatment of REGRESSIN® had no effect on its ability to stimulate IL-12 production.

These data show that M-DNA, as MCC, *M. phlei*-DNA or MCC-DNA, stimulates production of the cytokine IL-12 by murine macrophages. As with human lymphocytes (Example 7), MCC stimulates more IL-12 production than *M. phlei*-DNA or MCC-DNA and DNase I treatment significantly reduces MCC-DNA and MCC stimulated IL-12 production.

EXAMPLE 23

Effect of MCC, *M-phlei*-DNA, MCC-DNA and Regressin® on Nitric Oxide (NO) Production by Murine Peritoneal Macrophages Macrophage activation stimulates production of reactive oxygen species including, but not limited to, nitric oxide, superoxide radicals and hydroxyl radicals. These reactive oxygen species induce cytolysis and apoptosis in responsive cells and, therefore, have anti-cancer activity.

Murine peritoneal macrophages were incubated for 48 h with 0.1, 5.0 or 12.5 µg/ml of MCC, M-phlei-DNA, MCC-DNA and Regressin®. NO production was measured in nmol/L by reaction of $NO_2$—with Griess reagent using 100 µl of culture supernatant.

TABLE 12

Effect of MCC, M-phlei-DNA, MCC-DNA and Regressin ® on NO production by murine macrophages.
NO production, nmol/L

| Treatment | 12.5 µg/ml | 5.0 µg/ml | 0.1 µg/ml |
|---|---|---|---|
| M. phlei-DNA | 18.9 | 8.3 | 2.6 |
| MCC-DNA | Not Done | 3.0 | 1.8 |
| MCC | Not Done | 36.2 | Not Done |
| Regressin ® | 1.6 | 2.6 | 0.1 |

As shown in Table 12, at 5 µg/ml, MCC, stimulated significantly more NO production than M. phlei-DNA or MCC-DNA. Regressin®. Stimulated almost no NO production.

Murine macrophages were incubated for 48 h with 1 µg/ml MCC, DNase I treated MCC, MCC-DNA and M. phlei-DNA

TABLE 13

Stimulation of NO production in murine macrophages by MCC, DNase I treated MCC, MCC-DNA and M. phlei-DNA

|  | Experiment #1 NO (nmol/ml) | Experiment #2 NO (nmol/ml) |
|---|---|---|
| MCC | 43.7 | 30.7 |
| MCC + DNase I (1 U) | 0.0 | 2.1 |
| MCC-DNA | 2.6 | 2.1 |
| M. phlei-DNA | 0.0 | 1.6 |

As shown in Table 13, MCC stimulated significant NO production. DNase I treatment of MCC, which digests he M-DNA, abolished MCC stimulation of NO production. MCC-DNA and M. phlei-DNA stimulated minimal NO production.

These data suggest that, for optimal stimulation of NO production by macrophages, M-DNA must be presented to the macrophages complexed on a carrier such as M. phlei-cell wall.

Figure 16:
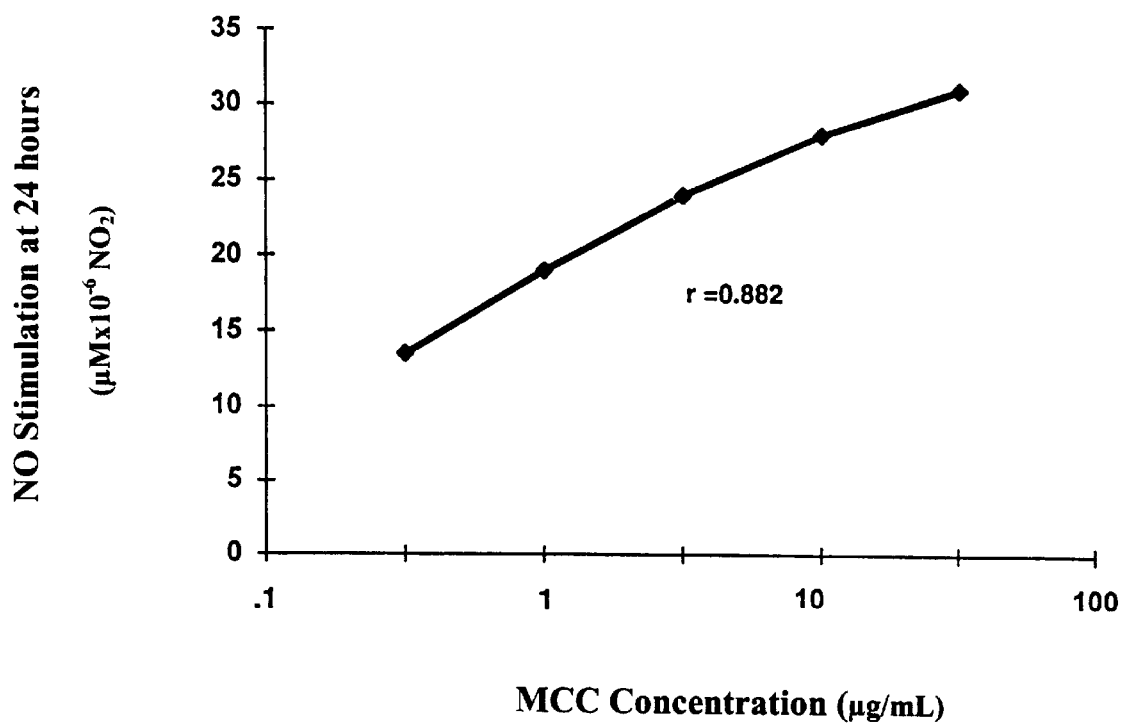
FIG. 16. Stimulation of NO production in RAW 264.7 monocytes by MCC.

EXAMPLE 24
Effect of MCC on the Production of Nitric Oxide (NO) by Murine RAW 264.7 Monocytes Murine RAW 264.7 monocytes were incubated for 24 h with increasing concentrations of MCC. Increasing concentrations of MCC stimulated increasing amounts of NO production (FIG. 16). This was unexpected as receptors for NO induction are not optimally expressed on monocytes and, therefore, NO production is not usually associated with monocytes. Under the same conditions, Regressin® did not stimulate NO production.

EXAMPLE 25
Stimulation of Cytokine Synthesis in vivo

Figure 17A:
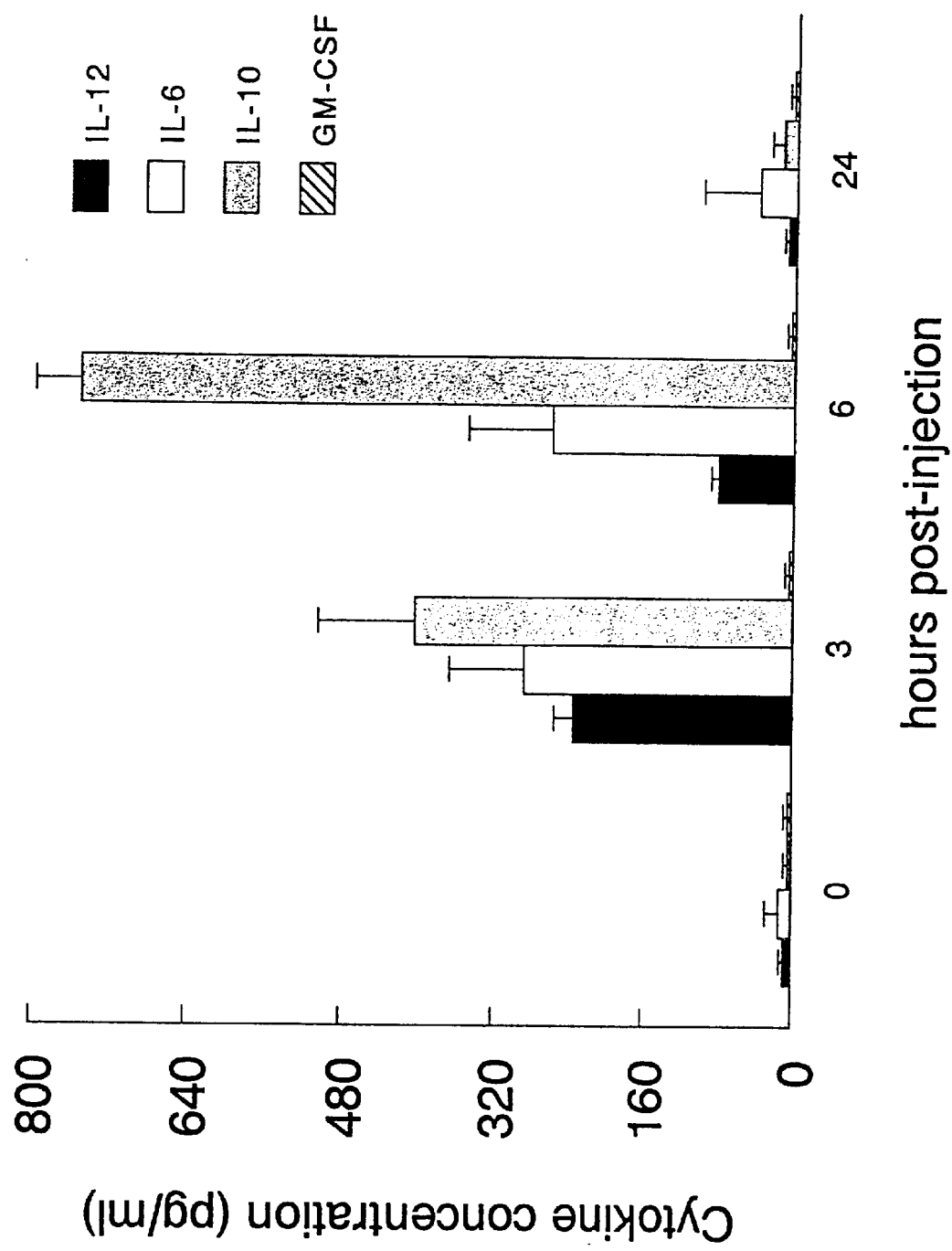
FIGS. 17A and 17B. In vivo stimulation of cytokine production in CD-1 mice by intra-peritoneal administration of MCC (17A) and intra-venous administration of MCC (17B).

Four groups of CD-1 mice, each containing 5 mice, were injected intraperitoneally with 50 mg/kg of MCC. Blood was collected at 0, 3, 6 and 24 h after injection and concentrations (pg/ml) of IL-6, IL-10, IL-12 and GMSF in the sera were determined at 0, 3, 6 and 24 h post-injection (FIG. 17A). With intraperitoneal MCC, sera concentrations of IL-6, IL-10 and IL-12 were significantly increased at 3 and 6 h post-injection, and declined to approximately control values (0 h) at 24 h post injection. Sera concentrations of GM-CSF remained at about control values (0 h) at 3, 6 and 24 h post-injection.

Figure 17B:
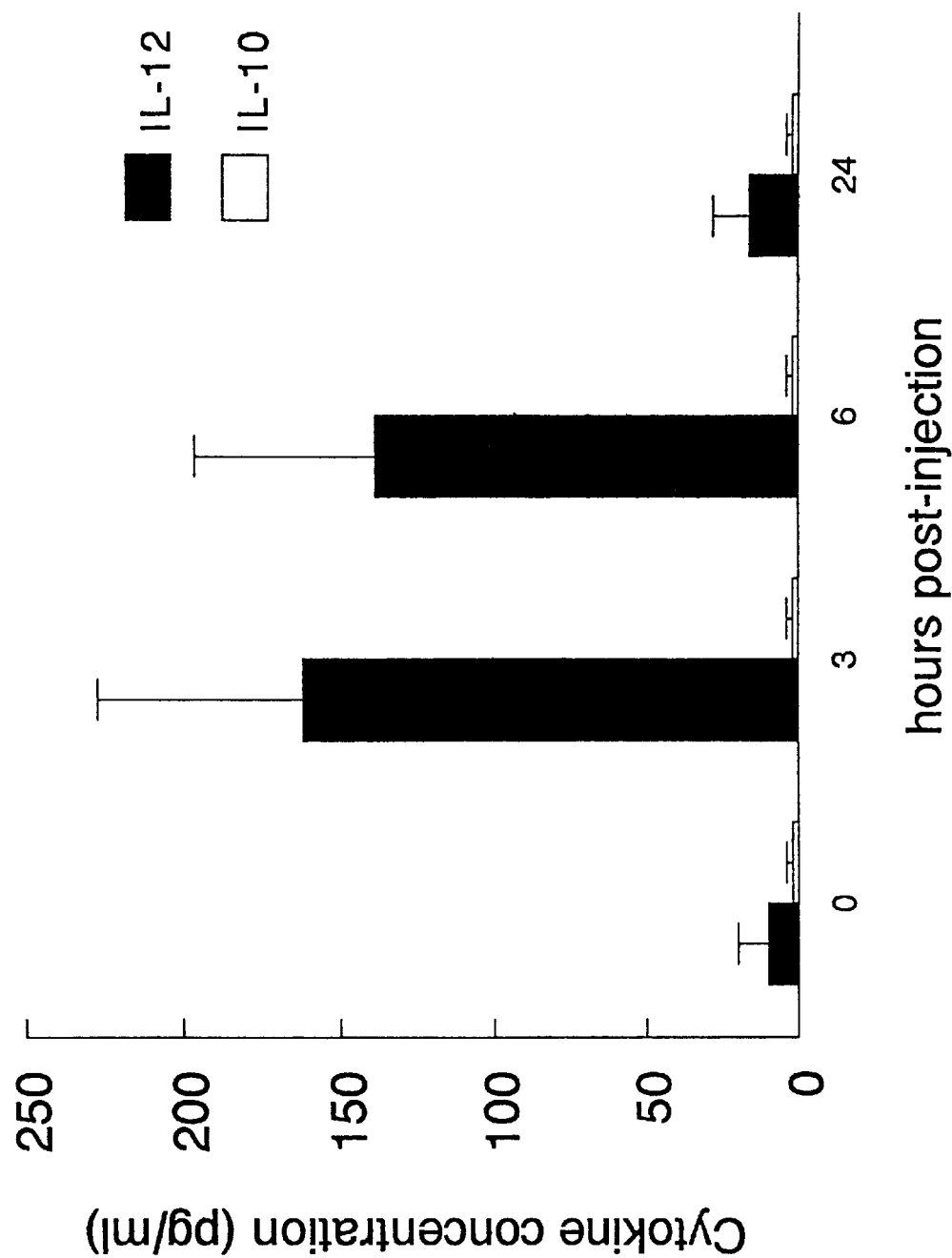

Five groups of CD-1 mice, each containing 5 mice, were injected intravenously with 6.6 mg/kg of MCC. Blood was collected at 0, 3, 6 and 24 h after injection and concentrations (pg/ml) of IL-10 and IL-12 in the sera were determined at 0, 3, 6 and 24 h post-injection (FIG. 17B). With intravenous MCC, sera concentrations of IL-12 were significantly increased at 3 and 6 h post-injection, and declined to approximately control values (0 h) at 24 h post injection. Sera concentrations of IL-10 remained at about control values (0 h) at 3, 6 and 24 h post-injection.

These data demonstrate that in vivo administration of MCC stimulates production of the anti-cancer cytokines IL-6, IL-10 and IL-12, but not the pro-cancer cytokine GM-CSF. Further, these data demonstrate that the amount of MCC administered and the route of administration effect the activity of the MCC.

Four groups of CD-1 mice, each containing 4 mice, were injected intraperitoneally with untreated and with DNase I-treated MCC, and M. phlei-DNA. After 3 h, the mice were sacrificed, blood was collected by cardiac micropuncture and the concentration (pg/ml) of IL-12 in sera was measured.

TABLE 14

Effect of MCC and of M. Phlei-DNA ± DNase on IL-12 production in pg/ml by CD-1 mice

| | MCC | | MCC + DNase | % inhibition |
|---|---|---|---|---|
| mouse #1 | 255 | mouse #5 | 126 | 49% |
| mouse #2 | 180 | mouse #6 | 57 | 68% |
| mouse #3 | 146 | mouse #7 | 121 | 17% |
| mouse #4 | 199 | mouse #8 | 143 | 28% |
| average | 195 ± 46 | | 111 ± 38 | 40.5 ± 22.6% |

| | M. phlei-DNA | | M. phlei-DNA + DNase | % inhibition |
|---|---|---|---|---|
| mouse #9 | 135 | mouse #13 | 110 | 19% |
| mouse #10 | 283 | mouse #14 | 146 | 48% |
| mouse #11 | 118 | mouse #15 | 121 | 82% |
| mouse #12 | 270 | mouse #16 | 169 | 37% |
| average | 195 ± 46 | | 111 ± 38 | 46.5 ± 26.5% |

As shown in Table 14, in vivo administration of MCC and of M. phlei-DNA stimulate production of the anti-cancer cytokine IL-12. After DNase I treatment, MCC stimulated IL-12 production decreased 40.5% and M. phlei-DNA stimulated IL-12 production decreased 46.5%. This demonstrates that the oligonucleotide structure of M-DNA must be preserved for optimal stimulation of IL-12 production in vivo.

EXAMPLE 26
MCC Stability

MCC at 1 mg/ml was stored as a sterile suspension in 0.85% w/v NaCl in the dark at 4° C. or 6 months. Mean particle diameter was calculated using photon correlation spectroscopy (N4 Plus, Coulter Electronics Inc.). The MCC suspension was diluted with 0.85% w/v NaCl to a particle count rate between $5 \times 10^4$ and $10^6$ counts/sec. Mean particle diameter was calculated in size distribution processor mode (SDP) using the following conditions: fluid refractive index 1.33, temperature 20° C., viscosity 0.93 centipoise, angle of measurement 90.0°, sample time 10.5 μs, and sample run time 100 sec. Potential, the electric charge at the hydrodynamic interface between the particles and the bulk solvent, was measured in a Delsa 440SX (Coulter Electronics Inc.) using the following conditions: current 0.7 mA, frequency range 500 Hz, temperature 20° C., fluid refractive index 1.33, viscosity 0.93 centipoise, dielectric constant 78.3, conductivity 16.7 ms/cm, on time 2.5 sec, off time 0.5 sec, and sample run time 60 sec.

Figure 18:
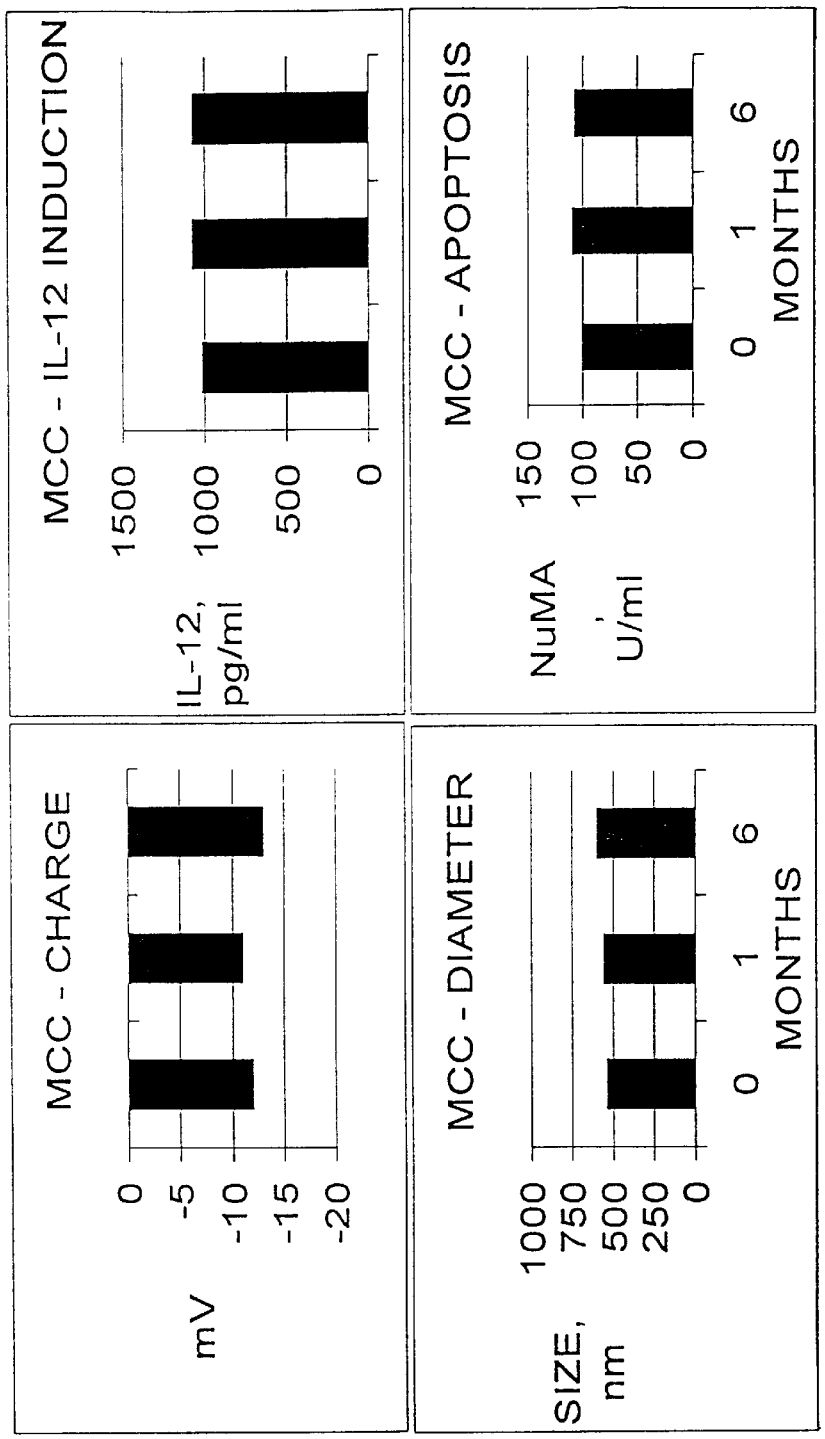
FIG. 18 Stability of MCC during 6 months of storage.

As shown in FIG. 18, MCC charge and MCC diameter remained relatively unchanged during 6 months of storage. Moreover, the MCC stimulation of IL-12 production and induction of apoptosis in THP-1 monocytes remained unchanged during 6 months of storage.

EXAMPLE 27
MCC and MCC-DNA Treatment of Human Bladder Cancer in nu/nu Mice

Human bladder cancer (HT-1197) is established as an ectopic solid tumor in the subcutaneous tissues of immunodeficient athymic nude mice (nu/nu mice) and the mice are divided into 5 groups. Group 1 receives vehicle alone. Group 2 receives MCC. Group 3 receives DNase I treated MCC. Group 4 receives MCC-DNA. Group 5 receives DNase I treated MCC-DNA. Cancer mass is measured before treatment and weekly during 4 weeks of treatment. Group 2 mice and Group 4 mice show regression of cancer mass.

EXAMPLE 28
MCC Treatment of Human Bladder Cancer

Ten patients with stage 3 orthotopic bladder cancer are divided into 2 groups. Group 1 receives intravesical instillation of MCC weekly for 8 weeks. Group 2 receives standard chemotherapy treatment. Group 1 patients show significant regression of bladder cancer and report no debilitating side effects. Group 2 patients show minimal regression of bladder cancer and report significant debilitating side effects.

EXAMPLE 29
Suspension in Aqueous Buffer

Lyophilized MCC is suspended in a pharmaceutically acceptable buffer and is emulsified by sonication at 20% output for 5 minutes (Model W-385 Sonicator, Heat Systems-Ultrasonics Inc). Optionally, the emulsified mixture is homogenized by microfluidization at 15,000–30,000 psi for one flow-through (Model M-110Y; Microfluidics, Newton, Mass.). The suspension is either processed under aseptic conditions or is sterilized by autoclaving.

EXAMPLE 30
Emulsification of MCC in Neutral Lipid

DNase free phosphatidylcholine is added to DNase free triglyceride soybean oil at a ratio of 1 gram of phospholipid to 20 ml of triglyceride and is dissolved by gentle heating at 50°–60° C. Several grams of MCC are added to a dry autoclaved container and the phospholipid-triglyceride solution is added at a concentration of 20 ml per 1 gram of MCC. The suspension is incubated for 60 min. at 20° C. and is then mixed with DNase-free PBS in the ratio of 20 ml MCC suspension per liter of PBS. The mixture is emulsified by sonication at 20% output for 5 minutes (Model W-385 Sonicator, Heat Systems-Ultrasonics Inc.). Optionally, the emulsified MCC mixture is homogenized by microfluidization at 15,000–30,000 psi for one flow-through (Model M-110Y; Microfluidics). The MCC emulsion is transferred to an autoclaved, capped bottle for storage at 4° C.

It should be understood, of course, that the foregoing relates only to a preferred embodiment of the present invention and that numerous modifications or alterations may be made therein without departing from the spirit and the scope of the invention as set forth in the appended claims.

We claim:

1. A method for inhibiting the growth of cancer cells in the urinary bladder of a mammal having bladder cancer, wherein a composition comprising:
   a. *Mycobacterium phlei* (*M. phlei*) deoxyribonucleic acid (M-DNA);
   b. deproteinized, delipidated mycobacterial cell wall, wherein the M-DNA is preserved and complexed on the *M. phlei* cell wall (MCC); and
   c. a pharmaceutically acceptable carrier, is instilled into the bladder of the mammal having the cancer in an amount effective to inhibit the growth of the cancer cells in the urinary bladder of the mammal having the bladder cancer.

2. The method of claims 1, wherein the gowth of the cancer cells is inhibited by stimulation of immune system cells to produce bioactive molecules.

3. The method of claim 2, wherein the bioactive molecules are selected from the group consisting of cytokines and reactive oxygen species.

4. The method of claim 3, wherein the cytokines are selected from the group consisting of IL-6, IL-10 and IL-12.

5. The method of claim 4, wherein the cytokines is IL-12.

6. The method of claim 1, wherein the growth of the cancer cells is inhibited by induction of apoptosis in the cancer cells.

7. The method of claim 2, wherein the induction of apoptosis is independent of abnormal Fas.

8. The method of claim 2, wherein the induction of apoptosis is independent of abnormal p53/p21.

9. The method of claim 2, wherein the induction of apoptosis is independent of drug resistance.

10. The method of claim 1, wherein the pharmaceutically acceptable carrier is selected from the group consisting of liquid carrier and a solid carrier.

11. The method of claim 1, wherein the growth of the cancer cells is inhibited by inhibition of proliferation of the cancer cells.

12. The method of claim 1, wherein the growth of the cancer cells is inhibited by activation of caspases in the cancer cells.

13. A method for inhibiting the growth of cancer cells in the urinary bladder of a mammal having bladder cancer, wherein a composition comprising:
  a. *Mycobacterium phlei* (*M. phlei*) deoxyribonucleic acid (M-DNA) and
  b. a pharmaceutically acceptable carrier, is instilled into the bladder of the mammal having the cancer in an amount effective to inhibit the growth of the cancer cells in the urinary bladder of the mammal having the bladder cancer.

14. The method of claim 13, wherein the pharmaceutically acceptable carrier is selected from the group consisting of liquid carrier and a solid carrier.

15. The method of claim 13, wherein the growth of the cancer cells is inhibited by induction of apoptosis in the cancer cells.

16. The method of claim 15, wherein the induction of apoptosis is independent of abnormal Fas.

17. The method of claim 15, wherein the induction of apoptosis is independent of abnormal p53/p21.

18. The method of claim 15, wherein the induction of apoptosis is independent of drug resistance.

19. The method of claims 13, wherein the growth of the cancer cells is inhibited by stimulation of immune system cells to produce bioactive molecules.

20. The method of claim 19, wherein the bioactive molecules are selected from the group consisting of cytokines and reactive oxygen species.

21. The method of claim 20, wherein the cytokines are selected from the group consisting of IL-6, IL-10 and IL-12.

22. The method of claim 21, wherein the cytokine is IL-12.

23. The method of claim 13, wherein the growth of the cancer cells is inhibited by inhibition of proliferation of the cancer cells.

24. The method of claim 13, wherein the growth of the cancer cells is inhibited by activation of caspases in the cancer cells.

* * * * *

UNITED STATES PATENT AND TRADEMARK OFFICE
CERTIFICATE OF CORRECTION

PATENT NO. : 6,329,347 B1
DATED : December 11, 2001
INVENTOR(S) : Phillips et al.

Page 1 of 1

It is certified that error appears in the above-identified patent and that said Letters Patent is hereby corrected as shown below:

Column 10,
Line 17, please delete "BACTO®" and insert therefor -- , BACTO®, --.

Column 12,
Line 12, please delete "Regressin" and insert therefor -- REGRESSIN --.
Line 14, please delete "Tween 80" and insert therefor -- TWEEN 80 --.

Column 20,
Line 7, please delete "Regressin" and insert therefor -- REGRESSIN --.

Column 26,
Line 56, please delete "claims" and insert therefor -- claim --.
Line 56, please delete "gowth" and insert therefor -- growth --.
Line 64, please delete "cytokines" and insert therefor -- cytokine --.

Column 27,
Line 9, before "liquid carrier" insert -- a --.
Line 28, before "liquid carrier" insert -- a --.

Column 28,
Line 10, please delete "claims" and insert therefor -- claim --.

Signed and Sealed this

Seventh Day of May, 2002

*Attest:*

*Attesting Officer*

JAMES E. ROGAN
*Director of the United States Patent and Trademark Office*

```
SEQUENCE LISTING

<160> NUMBER OF SEQ ID NOS: 1

<210> SEQ ID NO: 1
<211> LENGTH: 15
<212> TYPE: DNA
<213> ORGANISM: Unknown
<220> FEATURE:
<223> OTHER INFORMATION: Description of Artificial Sequence: synthetic

<400> SEQUENCE: 1
gctagacgtt agcgt                                                          15
```